(12) United States Patent
Kaiga

(10) Patent No.: US 8,658,096 B2
(45) Date of Patent: Feb. 25, 2014

(54) RACK TRANSPORT SYSTEM

(75) Inventor: Masahiro Kaiga, Shizuoka (JP)

(73) Assignee: Beckman Coutler, Inc., Brea, CA (US)

( * ) Notice: Subject to any disclaimer, the term of this patent is extended or adjusted under 35 U.S.C. 154(b) by 46 days.

(21) Appl. No.: 13/133,764

(22) PCT Filed: Mar. 23, 2009

(86) PCT No.: PCT/JP2009/055609
§ 371 (c)(1),
(2), (4) Date: Jun. 9, 2011

(87) PCT Pub. No.: WO2010/067633
PCT Pub. Date: Jun. 17, 2010

(65) Prior Publication Data
US 2011/0250091 A1    Oct. 13, 2011

(30) Foreign Application Priority Data
Dec. 11, 2008    (JP) .................................. 2008-315940

(51) Int. Cl.
*G01N 35/04*    (2006.01)
*G01N 35/02*    (2006.01)

(52) U.S. Cl.
CPC ..................... *G01N 35/04* (2013.01); *G01N 35/026* (2013.01)
USPC ................. 422/65; 422/63; 422/561; 436/43; 436/47

(58) Field of Classification Search
None
See application file for complete search history.

(56) References Cited

U.S. PATENT DOCUMENTS 5,720,377 A    2/1998    Lapeus et al.

FOREIGN PATENT DOCUMENTS

| JP | 9-33540 A | | 2/1997 |
|---|---|---|---|
| JP | 09-196926 | * | 7/1997 |
| JP | 10-123146 | * | 5/1998 |
| JP | 10-123146 A | | 5/1998 |
| JP | 2000-162216 A | | 6/2000 |
| JP | 2001-272408 | * | 10/2001 |
| JP | 2001-272408 A | | 10/2001 |

OTHER PUBLICATIONS

The International Search Report from PCT/JP2009/055609, dated May 19, 2009 (English translation (2 pages), included).

* cited by examiner

*Primary Examiner* — P. Kathryn Wright
(74) *Attorney, Agent, or Firm* — Kilpatrick Townsend & Stockton LLP

(57) ABSTRACT

Provided is a rack transport system that horizontally slides a rack tray holding and storing a plurality of specimen containers, allowing the rack tray to be safely placed on a rack tray set section. For this purpose, a rack transport system (8) using a rack tray (10) having a rack dropout-preventing mechanism (10*b*) includes a rack tray set section (8A) that has a lock canceling mechanism (8*i*) of the rack dropout-preventing mechanism and on which the rack tray that arranges and holds a plurality of racks (9) supporting a plurality of specimen containers (9*a*) is placed, and a projection section (8*h*) serving as a lock canceling button of the rack dropout-preventing mechanism is formed at a position where the rack tray that holds and stores the plurality of racks supporting the plurality of specimen containers is slid to be able to be set in the rack tray set section.

20 Claims, 20 Drawing Sheets

RACK TRANSPORT SYSTEM

CROSS-REFERENCE TO RELATED APPLICATIONS

This application is a National Stage of International Application No. PCT/JP2009/055609, filed Mar. 23, 2009, which claims the benefit of priority to Japanese Application No. 2008-315940, filed Dec. 11, 2008, the disclosures of each are herein incorporated by reference.

TECHNICAL FIELD

The present invention relates to a rack transport system that transports a rack tray holding a plurality of racks.

BACKGROUND ART

In the past, a dispenser or an automatic analyzing apparatus employs a system that transports a plurality of racks by using a rack tray that can arrange and hold the plurality of racks supporting a plurality of a specimen containers when supplying or collecting a specimen (for example, see Patent Reference 1).

Patent Reference 1: Japanese Laid-Open Patent Publication No. 10-123146

DISCLOSURE OF THE INVENTION

Problem to be Solved by the Invention

However, a rack tray disclosed in Patent Reference 1 includes a rack dropout-preventing mechanism that prevents a rack to be stored from being dropped out when the rack tray is transported, and a rack tray set section of the rack transport system has a canceling mechanism of the rack dropout-preventing mechanism. However, since a lever of the canceling mechanism is arranged near a rack outlet port of the rack tray set section, the rack tray collides with a projection of a canceling lever when the rack tray is tried to be slid to be set in the tray placing section. For this reason, the rack tray needs to be placed from directly above. Thus, operability is very poor when a rack tray is being placed because a rack tray holding a plurality of specimen containers is heavy.

The present invention has been made in consideration of the above description and has as its objective to provide a rack transport system that horizontally slides a rack tray holding and storing a plurality of specimen containers to make it possible to safely place the rack tray on a rack tray set section.

Means for Solving the Problem

In order to solve the problem and to achieve the objective, a rack transport system according to the present invention is a rack transport system using a rack tray having a rack dropout-preventing mechanism including a dropout-preventing lever, a shaft that supports the dropout-preventing lever on a rack tray, and a spring that biases the dropout-preventing lever upward about the shaft to cause the dropout-preventing lever to project from a rack tray opening to prevent a rack from dropping out, the system characterized by including: a rack tray set section that has a lock canceling mechanism of the rack dropout-preventing mechanism and on which the rack tray that arranges and holds a plurality of racks supporting a plurality of specimen containers is placed; a rack collecting section on which an empty rack tray is placed and the rack collecting section collects the racks supporting the specimen containers obtained after a dispensing operation is performed; and a transporting mechanism that transports the rack from the rack tray set section to a dispensing mechanism and transports the rack to the rack collecting section after a specimen is dispensed from the specimen container, wherein a lock canceling button of the lock canceling mechanism is formed at a position where the rack tray that holds and stores the plurality of racks supporting the plurality of specimen containers is slid to be able to be set in the rack tray set section.

The rack transport system according to the present invention, in the above invention, is characterized in that the rack tray set section includes a storing section that stores a rack tray, and the rack tray is slid from an upper side of a guide wall behind the storing section and placed on the rack tray set section.

The rack transport system according to the present invention, in the above invention, is characterized in that the lock canceling button is formed near the guide wall behind the rack tray set section.

The rack transport system according to the present invention, in the above invention, is characterized in that the dropout-preventing lever has a length almost equal to a length of the rack tray in a rack traveling direction.

The rack transport system according to the present invention, in the above invention, is characterized in that the lock canceling mechanism includes a lock canceling lever having a length almost equal to a length of the rack tray set section in a rack traveling direction, a shaft that supports the lock canceling lever on the rack tray set section, and a spring that biases a lock canceling lever end on a guide wall side behind the rack tray set section to push up the lock canceling lever end, both ends of the lock canceling lever have projection sections that vertically rise, the projection section on the guide wall side behind the rack tray set section is the lock canceling button, and a hole to protrude the projection section therethrough is formed in the rack tray storing section of the rack tray set section.

The rack transport system according to the present invention, in the above invention, is characterized in that the spring biases the lock canceling lever end on the guide wall side behind the rack tray set section to push up the lock canceling lever end to protrude the projection from the hole, and, when the rack tray that holds and stores a plurality of racks is slid to be placed on the rack tray set section, the projection section is pushed down by placing the rack tray, and the projection section at the other end is pushed up to cancel the lock state of the rack movement-preventing mechanism.

The rack transport system according to the present invention, in the above invention, is characterized in that the lock canceling mechanism includes a lock canceling lever arranged on a side of the transporting mechanism of the rack tray set section, a sensor that is arranged near the guide wall behind the rack tray set section and, when the rack tray that holds and stores a plurality of racks is slid and placed on the rack tray set section, detects the placement, and a motor that pushes up the lock canceling lever after the sensor detects the placement of the rack tray on the rack tray set section, wherein the sensor is the lock canceling button.

The rack transport system according to the present invention, in the above invention, is characterized in that the rack collecting section includes the lock canceling mechanism of the rack dropout-preventing mechanism.

The rack transport system according to the present invention, in the above invention, is characterized in that the rack tray includes a tray base that holds and stores a plurality of racks, and a rack movement-preventing mechanism that moves on the tray base and presses the plurality of racks arranged on the tray base to a side of the rack dropout-preventing mechanism.

The rack transport system according to the present invention, in the above invention, is characterized in that the rack tray includes a guide rail having a plurality of engagement sections at positions corresponding to the number of racks held and stored on the tray base, and a locking section held by the rack movement-preventing mechanism is engaged with the engagement section to lock the movement of the rack in the backward direction of the rack tray opening.

The rack transport system according to the present invention, in the above invention, is characterized in that the engagement section is a projection formed on the guide rail, an inclination of a slope on a side of the rack tray opening is set to be high, and an inclination of the other slope is to be low.

The rack transport system according to the present invention, in the above invention, is characterized in that the rack movement-preventing mechanism includes a handle section that pushes up the locking section, the handle section is gripped and pressed to push up the locking section to cancel the engagement with the engagement section, and the rack movement-preventing mechanism is moved.

The rack transport system according to the present invention, in the above invention, is characterized by comprising grip members on two opposite sides parallel to an arrangement direction of the racks on the tray base.

The rack transport system according to the present invention, in the above invention, is characterized in that the rack movement-preventing mechanism includes a shaft supported by the handle section and extending to a lower section of the guide rail, and the guide rail includes a trench section through which the shaft passes with movement of the rack movement-preventing mechanism.

The rack transport system according to the present invention, in the above invention, is characterized in that the guide rail is formed independently of the tray base, joined to the tray base by a joint member, and a spring that biases the guide rail to push up the guide rail is arranged between the joint member and the guide rail.

The rack transport system according to the present invention, in the above invention, is characterized in that the tray base includes guide walls on three sides except for the opening in the rack traveling direction, and a guide wall of anyone of two sides parallel to the traveling direction has a fitting section fitted on the rack formed on a side surface thereof.

The rack transport system according to the present invention, in the above invention, is characterized in that a rack having a projection section that is fitted in the fitting section of the guide wall is held and stored.

The rack transport system according to the present invention, in the above invention, is characterized in that the grip member arranged on an opening of the rack in the traveling direction is arranged such that a holding section is offset from an arrangement position of the grip member.

The rack transport system according to the present invention, in the above present invention, is characterized in that the rack collecting section includes a lock canceling mechanism of the rack movement-preventing mechanism.

The rack transport system according to the present invention, in the above invention, is characterized in that the lock canceling mechanism of the rack movement-preventing mechanism is a push-up member that pushes up the shaft of the rack tray.

The rack transport system according to the present invention, in the above invention, is characterized in that the lock canceling mechanism of the rack movement-preventing mechanism is a push-up member that pushes up the joint member of the rack tray to push down the guide rail.

Effect of the Invention

According to the present invention, since a lock canceling button that cancels the locking of a rack dropout-preventing mechanism is formed near a guide wall behind a rack tray set section to make it possible to slide and place a rack tray holding and storing a plurality of racks supporting a plurality of specimen containers on the rack tray set section, the rack transport system can be easily and safely operated.

BRIEF DESCRIPTION OF THE DRAWINGS

FIG. 5-1 is an operational diagram of a rack movement-preventing mechanism according to Embodiment 1.

FIG. 5-2 is an operational diagram of a rack movement-preventing mechanism according to Embodiment 1.

FIG. 8-1 is an operational diagram of the lock cancellation of the rack movement-preventing mechanism according to Embodiment 1.

FIG. 8-2 is an operational diagram of the lock cancellation of the rack movement-preventing mechanism according to Embodiment 1.

FIG. 12-1 is an operational diagram 1 of a series of operations of setting a rack tray in the rack tray set section according to Embodiment 1.

FIG. 12-2 is an operational diagram 2 of a series of operations of setting a rack tray in the rack tray set section according to Embodiment 1.

FIG. 12-3 is an operational diagram 3 of a series of operations of setting a rack tray in the rack tray set section according to Embodiment 1.

FIG. 12-4 is an operational diagram 4 of a series of operations of setting a rack tray in the rack tray set section according to Embodiment 1.

FIG. 13-1 is a front view showing Modification 1 of the rack tray according to Embodiment 1.

FIG. 13-2 is a pattern diagram showing a main part configuration of an automatic analyzing apparatus using the rack tray according to a modification of Embodiment 1.

FIG. 16-1 is a cross-sectional view of a rack tray according to Modification 3 of Embodiment 1 together with a rack and a rack collecting section.

FIG. 16-2 is a cross-sectional view of the rack tray according to Modification 3 of Embodiment 1 together with a rack and a rack collecting section.

Figure 1:
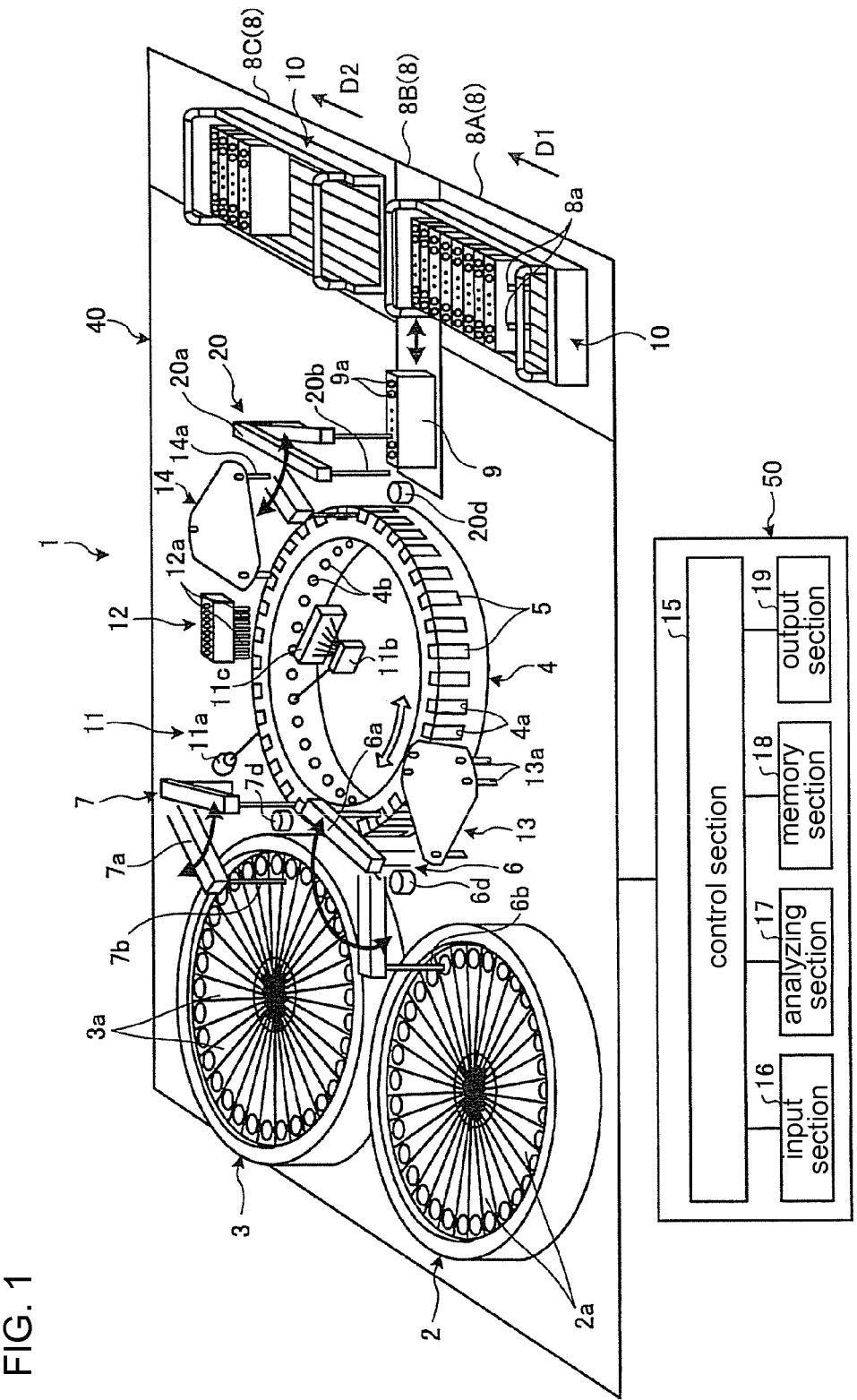
FIG. 1 is a pattern diagram showing a main part configuration of an automatic analyzing apparatus using a rack tray according to Embodiment 1.

1, 1A Automatic analyzing apparatus
2, 3 First and second reagent storage
2a, 3a Reagent container
4 Reaction table
4a Holding section
4b Optical path
5 Reaction container
6, 7 First and second reagent dispenser
6a, 7a Arm
6b, 7b Probe
8, 8' Rack transport system
8a Push-out lever
8c Rack tray storing section
8d Hole
8e Spring
8f Shaft
8g Lock canceling lever
8h, 8h' Projection section
8i Lock canceling mechanism
8k Guide wall
8A, 8A', 8A" Rack tray set section
8B, 8B' Transport mechanism
8C Rack collecting section
9, 9A Rack
9a Specimen container
10, 10A, 10B, 10C, 10D Rack tray
10a Tray base
10b, 10b' Rack dropout-preventing mechanism
10c, 10c', 10c" Rack movement-preventing mechanism
10d Grip member
10e, 10e' Guide rail
10f Guide wall
10g Substrate
10h, 61 Engagement section
8b, 10i, 10j Trench
10k, 10l, 10k', 10l' Partition
10m, 10r, 33 Spring
10n, 10q, 32 Shaft
10o E ring
10p, 60 Projection
10s, 10s' Dropout-preventing lever
10t, 10t' Push-up section
11 Analytical optical system
12 Cleaning mechanism
13, 14 First and second stirring device
15 Control section
16 Input section
17 Analyzing section
18 Memory section
19 Output section
20 Specimen dispenser
30 Joint member
31 Joint section
40 Measuring mechanism
50 Control mechanism

BEST MODE FOR CARRYING OUT THE INVENTION

With reference to the accompanying drawings, a rack transport system according to the embodiments of the present invention will be described below by using, as an example, an automatic analyzing apparatus that analyzes a liquid specimen such as blood as a sample. Drawings referred to in the following explanation are representative. When the same object is shown indifferent drawings, the dimensions, scales and the like of the object may be different from each other. The invention is not limited to the embodiments. In the drawings, the same parts are denoted by the same reference numerals.

Embodiment 1

FIG. 1 is a pattern diagram showing a configuration of an automatic analyzing apparatus 1 using a rack transport system 8 according to Embodiment 1. As shown in FIG. 1, the automatic analyzing apparatus 1 includes a measuring mechanism 40 that dispenses a specimen to be analyzed and a reagent into reaction containers 5, respectively, and optically measures reactions occurring in the reaction containers 5 into which the specimen and the reagent are dispersed, and a control mechanism 50 that controls the entire automatic analyzing apparatus 1 including the measuring mechanism 40 and analyzes measurement results in the measuring mechanism 40. The automatic analyzing apparatus 1 automatically performs biochemical, immunological, or genetical analysis of a plurality of specimens by the incorporation of the two mechanisms.

The measuring mechanism 40 includes a first reagent storage 2, a second reagent storage 3, a reaction table 4, a first reagent dispenser 6, a second reagent dispenser 7, a rack transport system 8, an analytical optical system 11, a cleaning mechanism 12, a first stirring device 13, a second stirring device 14, and a specimen dispenser 20.

In the first reagent storage 2, as shown in FIG. 1, a plurality of reagent containers 2a that store first reagents are arranged in a circumferential direction. The first reagent storage 2 is rotated by driving means (not shown) to transport the reagent containers 2a in the circumferential direction. The plurality of reagent containers 2a is filled with reagents depending on inspection items, respectively. Information recording media (not shown), on which information such as types, lots, expiration dates of the stored reagents are recorded, are stuck on outer surfaces of the reagent containers 2a. In this case, on a periphery of the first reagent storage 2, a reading device (not shown) that reads the reagent information recorded on the information recording medium stuck on the reagent container 2a and outputs the reagent information to a control section 15 is installed. Above the first reagent storage 2, an openable and closable lid (not shown) is arranged to suppress the reagent from being evaporated or transformed. A constant temperature tank (not shown) for cooling reagent is arranged below the first reagent storage 2.

In the second reagent storage 3, as shown in FIG. 1, a plurality of reagent containers 3a that store second reagents are arranged in a circumferential direction. Like the first reagent storage 2, the second reagent storage 3 is rotated by driving means (not shown) to transport the reagent containers 3a in the circumferential direction. The plurality of reagent containers 3a is filled with reagents depending on inspection items, respectively. Information recording media (not shown), on which information such as types, lots, expiration dates of the stored reagents are recorded, are stuck on outer surfaces of the reagent containers 3a. In this case, on a periphery of the second reagent storage 3, a reading device (not shown) that reads the reagent information recorded on the information recording medium stuck on the reagent container 3a and outputs the reagent information to the control section 15 is installed. Above the second reagent storage 3, an openable and closable lid (not shown) is arranged to suppress the reagent from being evaporated or transformed. A constant temperature tank (not shown) for cooling reagent is arranged below the second reagent storage 3.

On the reaction table 4, as shown in FIG. 1, a plurality of reaction containers 5 are arranged along a circumferential direction. The reaction table 4 is rotated by driving means (not shown) different from the driving means that drives the first and second reagent storages 2 and 3 in a direction indicated by an arrow to move the reaction container 5 in the circumferential direction. The reaction table 4 is arranged between a light source 11a and an optical splitter 11b and has a holding section 4a that holds the reaction container 5 and an optical path 4b formed by a circular opening that guides a beam emitted from the light source 11a to the optical splitter 11b. The holding sections 4a are arranged at predetermined intervals on the periphery of the reaction table 4 along a circumferential direction, and have the optical path 4b circumferentially extending on an inner circumferential side of the holding section 4a formed therein. An openable and closable lid (not shown) is arranged above the reaction table 4, and a constant temperature tank (not shown) to heat the reaction table 4 to a temperature at which a reaction between a specimen and a reagent is accelerated is arranged below the reaction table 4.

The reaction container 5 is a container, called a cuvette, shaped as a rectangular tube by an optically transparent material, for example, glass including heat-resistant glass, cyclic olefin, or polystyrene that transmits 80% or more of light included in light for analysis (340 to 800 nm) emitted from the analytical optical system 11.

The first reagent dispenser 6 includes an arm 6a that vertically moves and rotates about a vertical line passing through a proximal end of the arm 6a freely. At a distal end of the arm 6a, a probe 6b that sucks and discharges a specimen is attached. The first reagent dispenser 6 includes a breathing mechanism using a breathing syringe or a piezoelectric element (not shown). The first reagent dispenser 6 sucks the first reagent with the probe 6b from the reagent container 2a moved to a predetermined position on the first reagent storage 2 described above, swings the arm 6a in a clockwise direction in the drawing and discharges the first reagent into the reaction container 5 to perform a dispensing operation. On a pivotal trace of the probe 6b, a cleaning tank 6d that cleans the probe 6b with cleaning water is installed.

The second reagent dispenser 7 includes an arm 7a that vertically moves and rotates about a vertical line passing through a proximal end of the arm 7a freely. At a distal end of the arm 7a, a probe 7b that sucks and discharges a specimen is attached. The second reagent dispenser 7 includes a breathing mechanism using a breathing syringe or a piezoelectric element (not shown). The second reagent dispenser 7 sucks the second reagent with the probe 7b from the reagent container 3a moved to a predetermined position on the second reagent storage 3 described above, swings the arm 7a in a counterclockwise direction in the drawing and discharges the second reagent into the reaction container 5 to perform a dispensing operation. On a pivotal trace of the probe 7b, a cleaning tank 7d that cleans the probe 7b with cleaning water is installed.

The analytical optical system 11 is an optical system that causes light for analysis (340 to 800 nm) to transmit through a liquid sample in the reaction container 5 obtained by reaction between the reagent and the specimen to perform analysis, and has the light source 11a, the optical splitter 11b, and a light-receiving section 11c. The light for analysis emitted from the light source 11a transmits through the liquid sample in the reaction container 5 and is received by the light-receiving section 11c arranged at a position opposing the optical splitter 11b.

In the first and second stirring devices 13 and 14, stirring rods 13a and 14a stir the dispensed specimen and reagent to cause a uniform reaction.

In the cleaning mechanism 12, nozzle 12a sucks and discharges a reaction fluid in the reaction container 5 measured by the analytical optical system 11 and pours and sucks a cleaning solution such as a cleaner or a cleaning fluid to perform cleaning. Although the cleaned reaction container 5 is recycled, the reaction container 5 may be discarded depending on the inspection of contents after measurement is performed once.

The specimen dispenser 20 includes an arm 20a that vertically moves and rotates about a vertical line passing through a proximal end of the arm 20a freely. At a distal end of the arm 20a, a probe 20b that sucks and discharges a specimen is attached. The specimen dispenser 20 includes a breathing mechanism using a breathing syringe or a piezoelectric element (not shown). The specimen dispenser 20 sucks the specimen with the probe 20b from the specimen container 9a moved to a dispensing position by the rack transport system 8 (will be described below), swings the arm 20a in a clockwise direction in the drawing, and discharges the specimen into the reaction container 5 to perform a dispensing operation. On a pivotal trace of the probe 20b, a cleaning tank 20d that cleans the probe 20b with cleaning water is installed.

The rack transport system 8, as shown in FIG. 1, includes a rack tray set section 8A on which a rack tray 10 in which a plurality of racks 9 supporting a plurality of specimen containers 9a are arranged and held is placed, a rack collecting section 8C on which an empty rack tray 10 is placed and the rack collecting section collects a rack supporting a specimen container the dispensing operation of which is finished, and a transport mechanism 8B that transports the rack 9 pushed out of the rack tray set section 8A with a push-out lever 8a to the dispensing position of the specimen dispenser 20 and transports the rack 9 to the rack collecting section 8C after the specimen is dispensed by the specimen dispenser 20 from all the specimen containers 9a supported by the rack 9.

In order to supply the specimen container 9a to the specimen dispenser 20, the rack tray 10 is placed on the rack tray set section 8A, the plurality of racks 9 set in the rack tray 10 by the transport mechanism 8B are transported by the push-out lever 8a in a first direction indicated by an arrow D1 to sequentially send the plurality of racks 9 to the transport mechanism 8B. The push-out lever 8a is transported by transporting means such as a belt conveyor (not shown). The transport mechanism 8B transports the rack 10 sent with the push-out lever 8a to the dispensing position of the specimen dispenser 20 while stepping the rack 10 along the transport mechanism 8B extending to the specimen dispenser 20. In the rack tray 10, before being arranged in the rack transport system 8, the rack dropout-preventing mechanism 10b projects into the opening of the rack tray 10 to prevent the rack 9 from being dropped out of the opening (see FIG. 2). However, when the rack tray 10 is arranged in the rack tray set section 8A, a projection section 8h (see FIG. 10) serving as a lock canceling button of the rack dropout-preventing mechanism on a rack tray set section 8A (will be described later) is depressed to cancel the lock state of the rack dropout-preventing mechanism, and the rack 9 can be transported with a push-out lever 8a from the opening to the transport mechanism 8B.

After the specimen is dispensed by the specimen dispenser 20 from the specimen container 9a supported by the rack 9, the transport mechanism 8B transports the rack 9 from the dispensing position of the specimen dispenser 20 to a position opposing the rack collecting section 8C. The rack 9 is pushed out of the transport mechanism 8B to the rack collecting section 8C with a push-out lever (not shown) in a direction indicated by an arrow D2 and collected by the rack tray 10. Like the rack tray set section 8A, the rack collecting section 8C includes the projection section 8h (see FIG. 7) serving as the lock canceling button of the rack dropout prevention canceling mechanism. When the empty rack tray 10 is set in the rack collecting section 8C, the rack dropout-preventing mechanism 10c is unlocked to make it possible to transport the rack 9 from the transport mechanism 8B to the rack collecting section 8C with a push-out lever (not shown).

The control mechanism 50 includes the control section 15, an input section 16, the analyzing section 17, a memory section 18, and an output section 19. The control section 15 is connected to each section included in the measuring mechanism 40 and the control mechanism 50. As the control section 15, a microcomputer or the like is used to control operations of each section. The control section 15 performs predetermined input/output control about information input/output in/from each constituent part and performs predetermined information processing on the information. The control section 15 controls operations of each section of the automatic analyzing apparatus 1 and, when an expiration date or the like of the reagent is out of a set range on the basis of the information read from the information recording medium, controls the automatic analyzing apparatus 1 to stop an analyzing operation or gives an alarm to an operator. The control section 15 also functions as a transport control section that controls an operation of the rack transport system 8.

The input section 16 is constituted by using a keyboard, a mouse, or the like and acquires various pieces of information required for an analysis of a specimen, instruction information of an analyzing operation from the outside. The analyzing section 17 arithmetically operates an absorbance or the like on the basis of a measurement result acquired from the analytical optical system 11 to perform a constituent analysis of a specimen or the like. The memory section 18 is configured to store various pieces of information including analysis results of the specimen or the like by using a hard disk that magnetically stores information and a memory that, when the automatic analyzing apparatus 1 executes processing, loads various programs related to that processing from the hard disk and electrically stores the various programs. The memory section 18 may include an auxiliary memory device that can read information stored in a storage medium such as a CD-ROM, a DVD-ROM, or a PC card. The output section 19 is configured by using a printer, a communication mechanism, or the like, and outputs various pieces of information including an analysis result of the specimen to notify a user.

In the automatic analyzing apparatus 1 configured as described above, after the first reagent dispenser 6 dispenses a first reagent in the reagent container 2a to the plurality of reaction containers 5 sequentially transported in line, the specimen dispenser 20 dispenses the specimen in the specimen container 9a, the second reagent dispenser 7 dispenses a second reagent in the reagent container 3a, and the analytical optical system 11 measures a spectroscopic intensity of a sample obtained by a reaction between a specimen and a reagent. The measurement result is analyzed by the analyzing section 18 to automatically perform a constituent analysis of the specimen or the like. The reaction container 5 that is transported after the measurement by the analytical optical system 11 is finished is cleaned by the cleaning mechanism 12 while the reaction container 5 is being transported, thereby a series of analyzing operations are continuously repeated.

Figure 2:
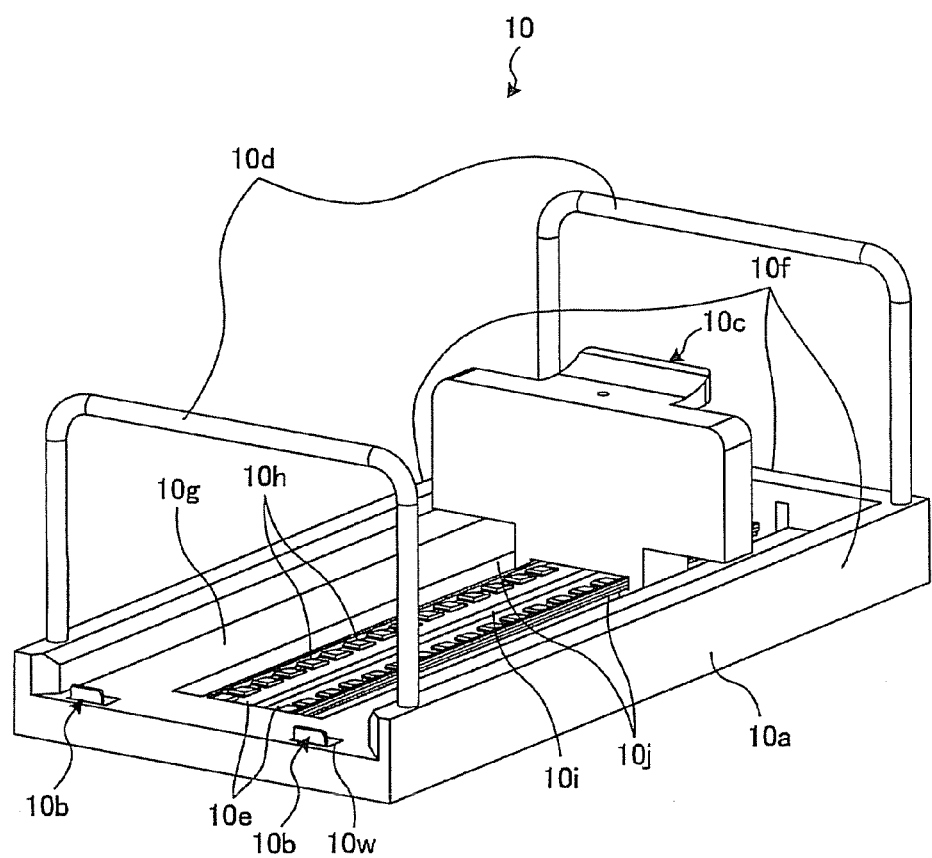
FIG. 2 is a perspective view of a rack tray according to Embodiment 1.

The rack tray 10 according to Embodiment 1 will be described below in detail with reference to FIG. 2. FIG. 2 is a perspective view of the rack tray 10 according to Embodiment 1. The rack tray 10 roughly includes a tray base 10a, a rack dropout-preventing mechanism 10b, a rack movement-preventing mechanism 10c, a grip member 10d, and a guide rail 10e. The tray base 10a has a substrate 10g supporting the rack 9, and guide walls 10f are arranged on three sides of the substrate 10g. The rack tray 10 has an opening in a side where the guide wall 10f is not formed, the rack dropout-preventing mechanism 10b projects into the opening to prevent the plurality of racks 9 stored on the tray base 10a from being dropped out of the opening. The grip members 10d are arranged on the opening and the guide wall 10f on the side opposing the opening, and a holding section of the grip member 10d is gripped to transport the rack tray 10. The grip member 10d shown in FIG. 2 vertically rises from the guide wall 10f and bends at the holding section to form an inverted U-shape. However, the grip member 10d arranged on the opening may have a bent section that can be horizontally bent outside the tray base 10a in the middle of a vertically rising pipe to make it possible to offset the holding section outside the rack tray 10. The grip member 10d is offset to make it easy to take in/out the rack 9. The guide rail 10e is integrated with the tray base 10a and formed in parallel to the traveling direction of the arranged and held racks 10. There is a trench 10i at a center section of the guide rail 10e and the trench 10i is provided for a shaft (will be described later) to travel. A plurality of engagement sections 10h are formed at positions corresponding to the number of racks to be stored on an upper surface of the guide rail 10e. The rack movement-preventing mechanism 10c is supported by the guide rail 10e by sandwiching the guide rail 10e from a side of a trench 10j (see FIG. 6). A projection 10p (see FIG. 4) serving as a locking section of the rack movement-preventing mechanism 10c (will be described later) is engaged with the engagement section 10h formed on the guide rail 10e to lock the rack movement-preventing mechanism 10c. In this manner, the held rack 9 is prevented from moving.

Figure 3:
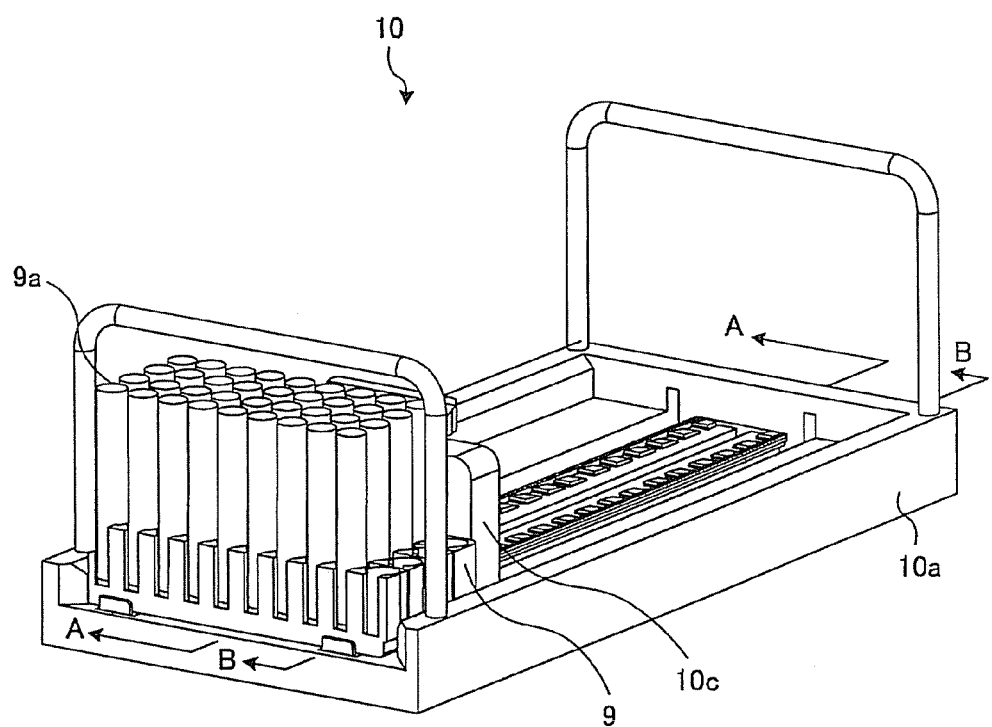
FIG. 3 is a perspective view of a rack tray that stores racks holding specimen containers.
Figure 4:
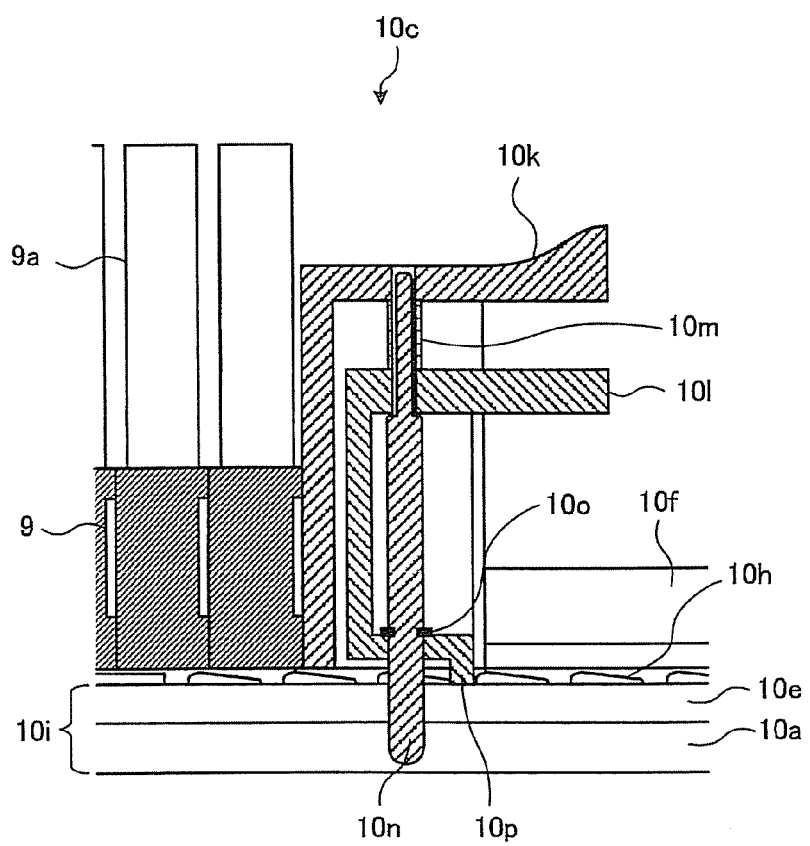
FIG. 4 is a sectional view of the rack tray shown in FIG. 3 along an A-A line.
Figures 1, 5:
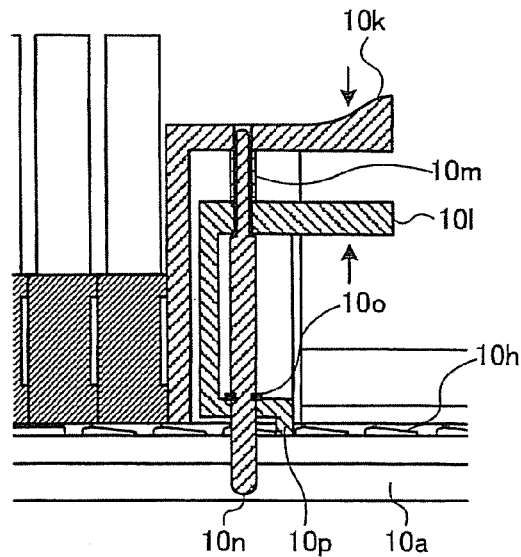
Figures 2, 5:
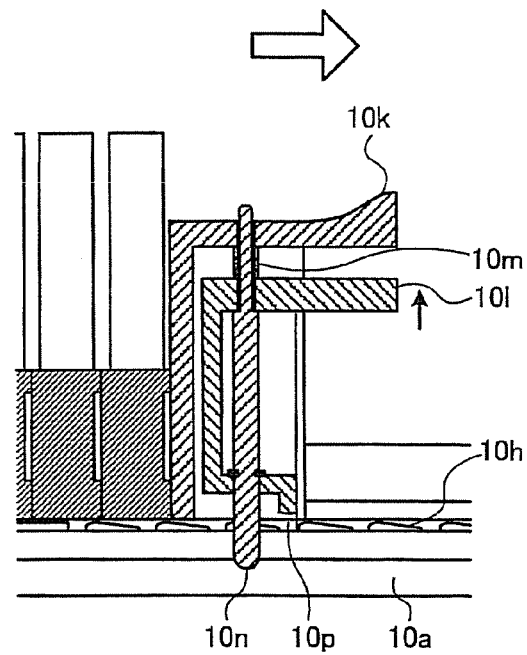
Figure 6:
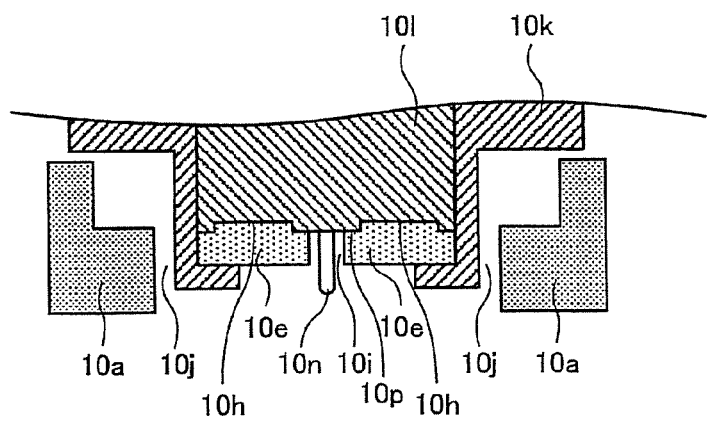
FIG. 6 is a cross-sectional view of an engagement section including the rack movement-preventing mechanism and a guide rail according to embodiment 1.

The rack movement-preventing mechanism 10c will be described below with reference to the drawing. FIG. 3 is a perspective view of the rack tray 10 in which the rack 9 holding the specimen container 9a is stored. FIG. 4 is a sectional view of the rack tray 10 in FIG. 3 along an A-A line. FIGS. 5-1 and 5-2 are operational diagrams of the rack movement-preventing mechanism 10c. FIG. 6 is a cross-sectional view of the engagement section including the rack movement-preventing mechanism 10c and the guide rail 10e.

As shown in FIG. 3, the racks 9 holding the specimen containers 9a are arranged in the tray base 10a of the rack tray 10 in parallel from the opening and pushed on an opening side by the rack movement-preventing mechanism 10c to prevent the rack 9 from moving and falling. As shown in FIG. 4, the rack movement-preventing mechanism 10c has a handle section including a partition 10k and a partition 10l, a push spring 10m is arranged between the partition 10k and the partition 10*l* to bias the partition 10*l* downward. The projection 10*p* is formed at a distal end of the partition 10*l*. The projection 10*p* is engaged between the plurality of engagement sections 10*h* arranged on the guide rail 10*e* at intervals each having a width of the rack 9 as one pitch. A shaft 10*n* extending to the lower section of the guide rail 10*e* is supported on the partition 10*l*, and an E ring 10*o* is attached between the shaft 10*n* and the partition 10*l*. In the movement of the rack movement-preventing mechanism 10*c*, the shaft 10*n* moves in the trench 10*i* formed between the guide rails 10*e* (see FIG. 2, FIG. 4, and FIG. 6). The shaft 10*n* serves a part of a lock canceling mechanism that cancels prevention of movement of the rack 9 by the rack movement-preventing mechanism 10*c* when the rack tray 10 is placed on the rack collecting section 8C.

The engagement section 10*h* is designed such that an inclination of a slope on the opening side in the traveling direction of the rack 9 is set to be high and an inclination of the other slope is set to be low. For this reason, in order to move the rack movement-preventing mechanism 10*c* on the opening side in the traveling direction, the partition 10*k* or the partition 10*l* serving as a handle section may be pushed. However, when the partition 10*k* or the partition 10*l* is pushed in the opposite direction, the rack movement-preventing mechanism 10*c* cannot be moved to a rear side of the opening opposing the traveling direction, and backward movement is locked because the inclination of the engagement section 10*h* on the opening side is high. In order to move the rack movement-preventing mechanism 10*c* in a forward or backward direction, as shown in FIG. 5-1, the partition 10*k* and the partition 10*l* serving as handle sections are gripped from the upper and lower sides and pushed. In this manner, the partition 10*l* is pushed up. When the partition 10*l* is pushed up, as shown in FIG. 5-2, the projection 10*p* at the distal end of the partition 10*l* rises. When the partition 10*l* is pushed up, the engagement between the projection 10*p* of the rack movement-preventing mechanism 10*c* and the engagement section 10*h* on the guide rail 10*e* is canceled to make it possible to move the rack movement-preventing mechanism 10*c* on the guide rail 10*e* to the rear side of the opening. The rack 9 held and stored on the rack tray 10 is prevented by the rack dropout-preventing mechanism 10*b* and the rack movement-preventing mechanism 10*c* from moving in a forward or backward direction and prevented by the opposite guide walls 10*f* of the rack tray 10 from moving side to side. However, since upward movement is not inhibited, a part of the rack 9 is pulled up to make it possible to freely pick any one of the stored racks 9 from an arbitrary position of the rack tray 10 without moving the rack movement-preventing mechanism 10*c*, and the rack 9 can be very easily taken in or out.

Figure 7:
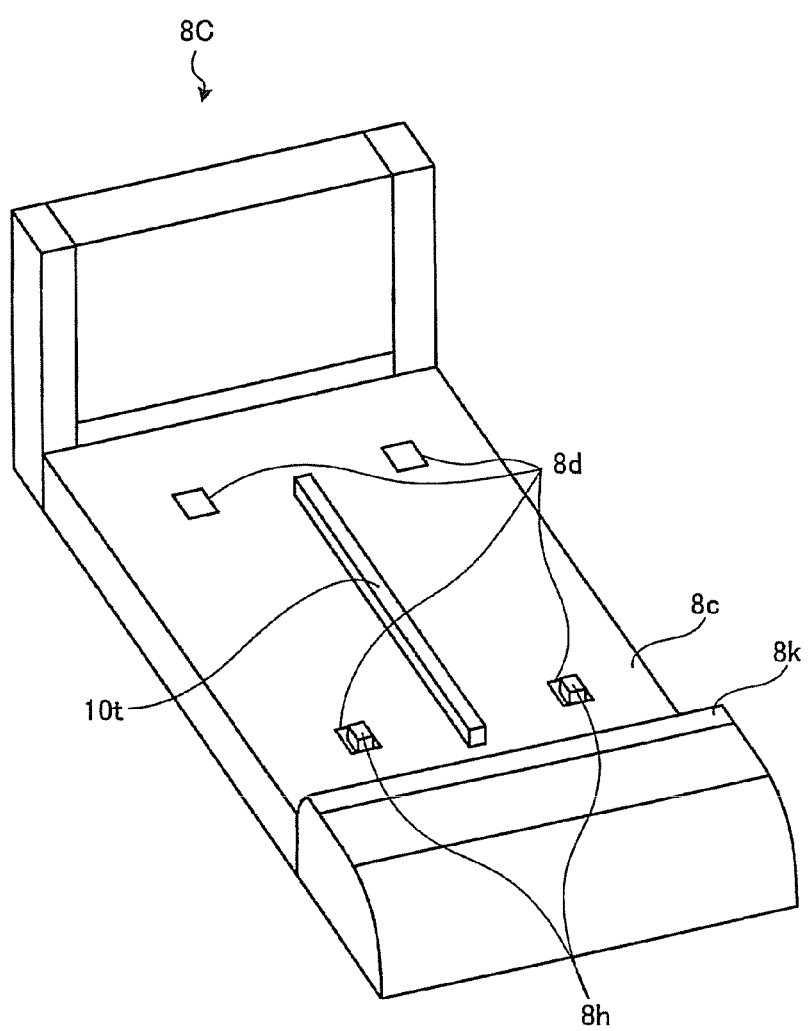
FIG. 7 is a perspective view of a rack collecting section according to Embodiment 1.
Figures 1, 8:
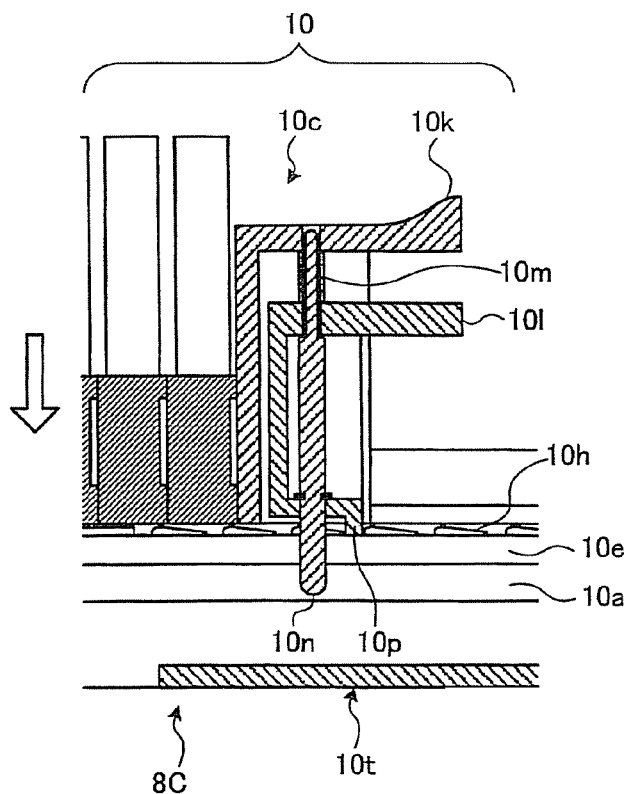
Figures 2, 8:
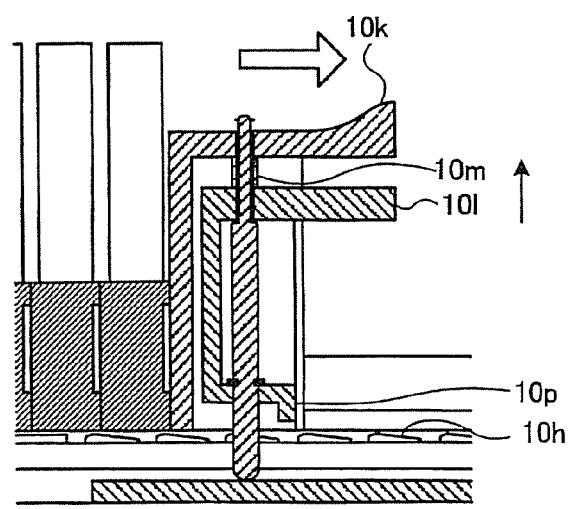

A lock canceling mechanism of the rack movement-preventing mechanism 10*c* will be described below with reference to FIG. 7, FIG. 8-1, and FIG. 8-2. FIG. 7 is a perspective view of the rack collecting section 8C. FIGS. 8-1 and 8-2 are operational diagrams of lock cancellation of the rack movement-preventing mechanism 10*c*. When the rack tray 10 is set on the rack collecting section 8C to collect the rack 9, the locked rack movement-preventing mechanism 10*c* hinders the rack 9 from being collected. Therefore, in order to save the trouble of manually moving the rack movement-preventing mechanism 10*c*, the lock canceling mechanism of the rack movement-preventing mechanism 10*c* is arranged. As shown in FIG. 7, the rack collecting section 8C includes a rack tray storing section 8*c*, a guide wall 8*k*, and a hole 8*d*, a push-up section 10*t* serving as a lock canceling mechanism of the rack movement-preventing mechanism 10*c* together with the shaft 10*n* is formed on the rack tray storing section 8*c*, and the projection section 8*h* serving as the lock canceling button of the rack dropout-preventing mechanism 10*b* (will be described later) projects from the hole 8*d*. The push-up section 10*t* is a narrow protrusion formed at a center section of the rack collecting section 8C in parallel to the rack traveling direction. As shown in FIG. 8-1, when the rack tray 10 is arranged on the rack collecting section 8C, the shaft 10*n* extending to the lower section of the guide rail 10*e* is brought into contact with the push-up section 10*t* on the rack collecting section 8C and pushed up. When the shaft 10*n* is pushed up, the partition 10*l* fixed to the shaft 10*n* is also pushed up. For this reason, as shown in FIG. 8-2, the projection 10*p* at the distal end of the partition 10*l* is lifted up to cancel the engagement with the engagement section 10*h* on the guide rail 10*e*. With the lock cancelling of the rack movement-preventing mechanism 10*c*, the rack movement-preventing mechanism 10*c* can be moved in a direction opposing the opening without gripping and pressing the partition 10*k* and the partition 10*l* serving as the handle sections from upper and lower sides. In this manner, the rack 9 is pushed to a side of the rack collecting section 8C with a push lever of the transport mechanism 8B, the unlocked rack movement-preventing mechanism 10*c* and the rack 9 are also moved in the direction opposing the opening of the rack tray 10.

Figure 9:
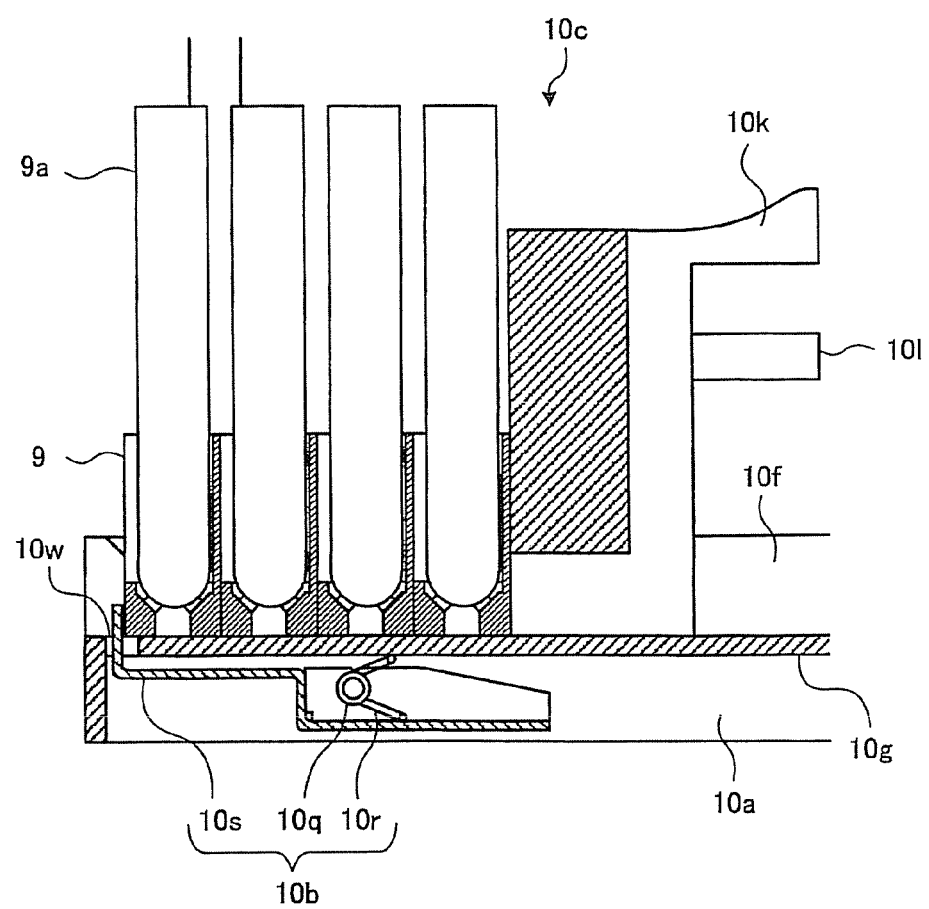
FIG. 9 is a sectional view of the rack tray shown in FIG. 3 along a B-B line.

The rack dropout-preventing mechanism 10*b* will be described below with reference to the drawings. FIG. 9 is a cross-sectional view of the rack tray 10 in FIG. 3 along a B-B line. As shown in FIG. 9, the rack dropout-preventing mechanism 10*b* has a dropout-preventing lever 10*s* that prevents the rack 9 from being dropped out of the opening. The step-like planar dropout-preventing lever 10*s* horizontally extends under the substrate 10*g* and bent from a hole 10*w* (see FIG. 2) formed near the opening and vertically rises up to prevent the rack 9 from being dropped out. The dropout-preventing lever 10*s* is supported on the tray base 10*a* with a shaft 10*q*, a spring 10*r* is set between the bottom surface of the substrate 10*g* and the dropout-preventing lever 10*s* to upwardly bias an end section of the dropout-preventing lever 10*s* rising up from the hole 10*w*. In FIG. 9, although a coil spring is used as the spring 10*r*, a leaf spring, a tension spring, or the like may be used.

Figure 10:
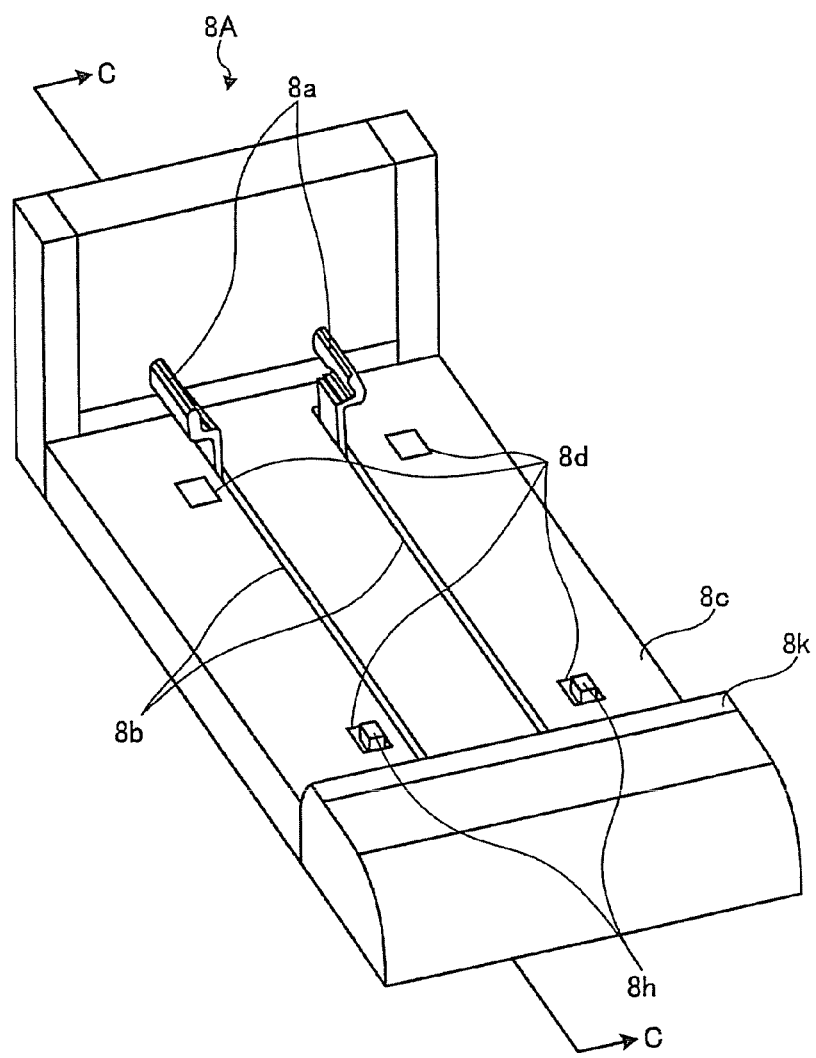
FIG. 10 is a perspective view of a rack tray set section according to Embodiment 1.
Figure 11:
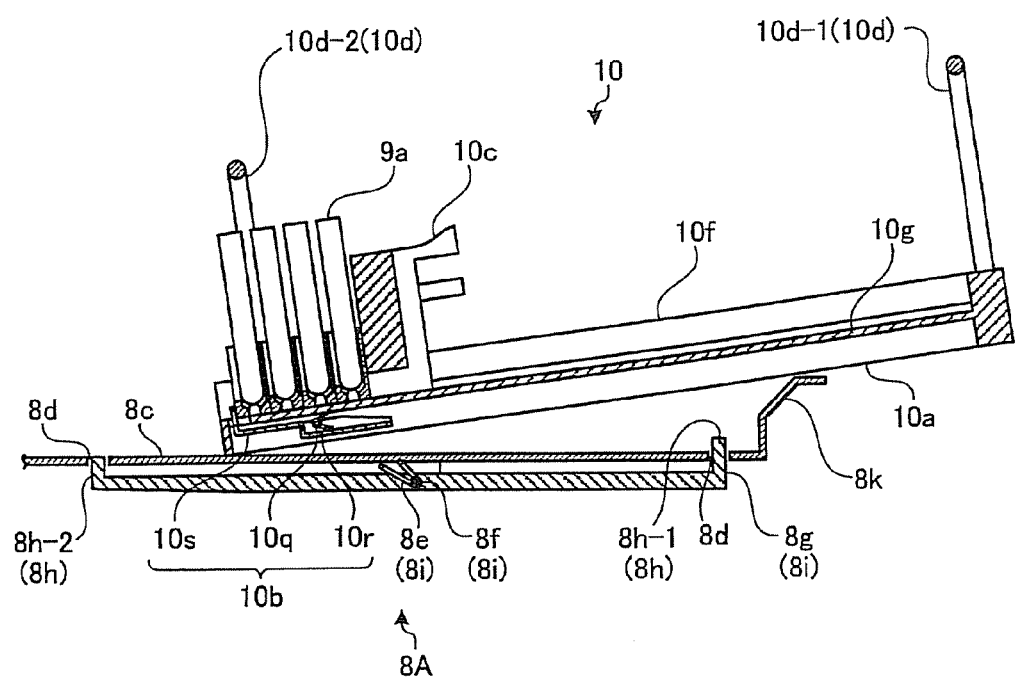
FIG. 11 is a cross-sectional view of the rack tray shown in FIG. 3 along a C-C line in the middle of placement of the rack tray on the rack tray set section in FIG. 10.

With reference to FIG. 10 and FIG. 11, the lock canceling mechanism of the rack dropout-preventing mechanism 10*b* will be described below. FIG. 10 is a perspective view of the rack tray set section 8A. FIG. 11 is a cross-sectional view of the rack tray set section 8A shown in FIG. 10 along a C-C line in the middle of placement of the rack tray 10 shown in FIG. 3 on the rack tray set section 8A. As shown in FIG. 10, the rack tray set section 8A includes the rack tray storing section 8*c*, the guide wall 8*k*, and the hole 8*d*. On the rack tray storing section 8*c*, the push-out lever 8*a* that pushes out the rack 9 on a side of the transport mechanism 8B is arranged, and the projection section 8*h* serving as the lock canceling button of the rack dropout-preventing mechanism 10*b* projects from the hole 8*d*. In Embodiment 1, since the rack dropout-preventing mechanisms 10*b* are formed at two positions (left and right), the projection sections 8*h* serving as the lock canceling buttons are also projected from two positions of the hole 8*d* near the guide wall 8*k*. The push-out lever 8*a* is generally built in the rack tray set section 8A before the rack tray 10 is arranged and travels through the trench 8*b* and the trench 10*j* of the rack tray 10 to push out the rack 9 on the opening side after the rack tray 10 is arranged.

As shown in FIG. 11, a lock canceling mechanism 8*i* of the rack dropout-preventing mechanism 10*b* arranged below the rack tray set section 8A includes a lock canceling lever 8*g*, a shaft 8*f*, and a spring 8*e*. The lock canceling lever 8*g* has a length almost equal to a length of the rack tray set section 8A in a rack traveling direction, and both the ends of the lock canceling lever 8g vertically rise to serve as projection sections 8h. The shaft 8f supports the lock canceling lever 8g in the rack tray set section 8C. The spring 8e biases a projection section 8h-1 on a guide wall side behind the rack tray set section 8A to push up the projection section 8h-1. In this manner, the projection section 8h-1 projects from the hole 8d on the rack tray storing section 8c. When a user places the rack tray 10 in which the plurality of racks 9 storing the specimen containers 9a are stored on the rack tray set section 8A, the user places the rack tray set 10 on a side of a grip member 10d-2 on which the racks 9 of the rack tray 10 are held and stored on the rack tray storing section 8c of the rack tray set section 8A, set the bottom section of the rack tray 10 on a side of a grip member 10d-1 on the guide wall 8k, and grips and presses the grip member 10d-1 to slide the rack tray 10 on the rack tray storing section 8c and set the rack tray 10 in the rack tray set section 8A.

Figures 1, 12:
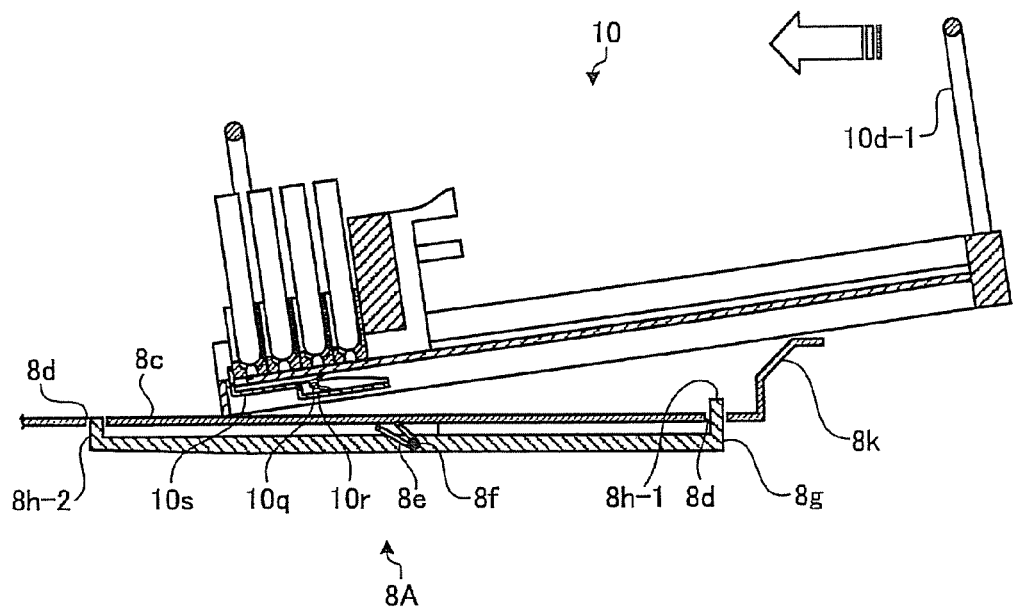
Figures 2, 12:
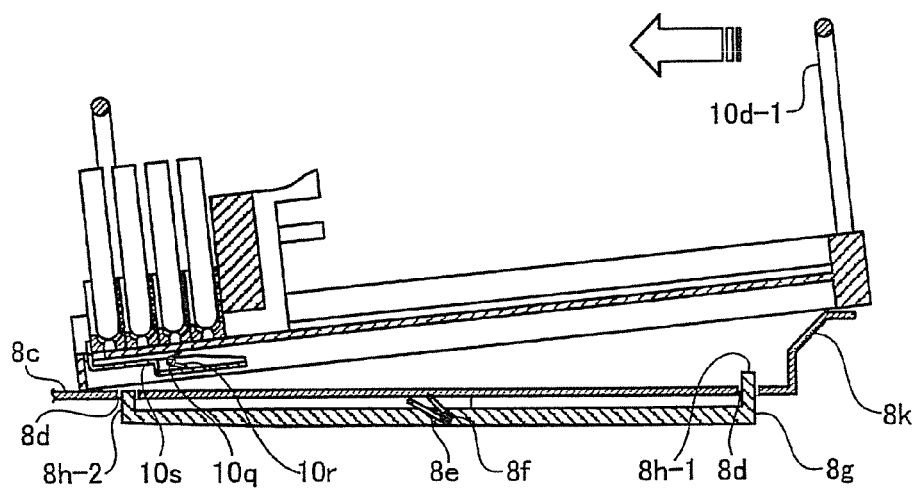
Figures 3, 12:
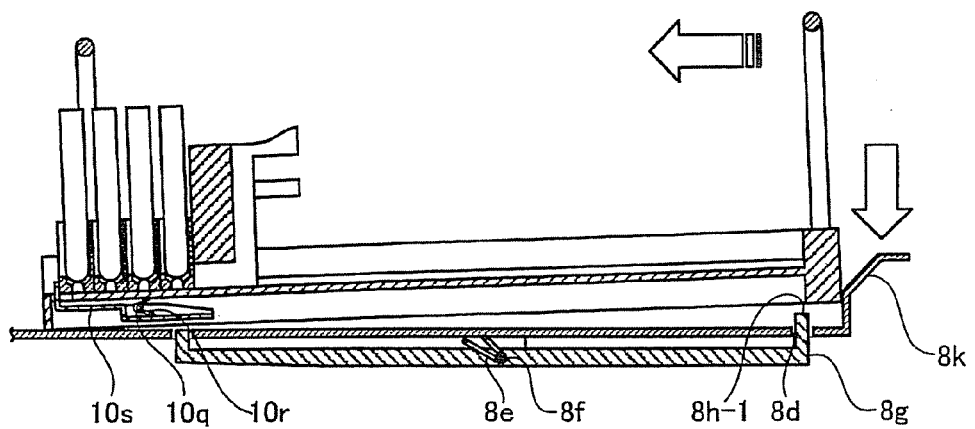
Figures 4, 12:
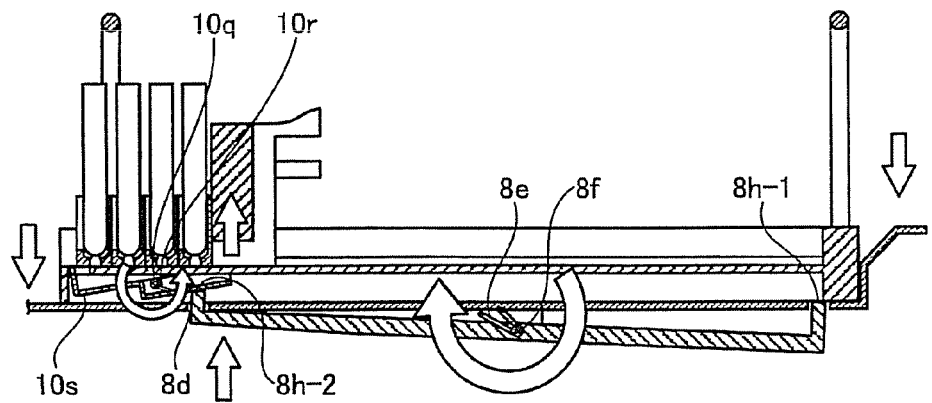

FIGS. 12-1 to 12-4 are operational diagrams of a series of operations of setting the rack tray 10 in the rack tray set section 8A. When the rack tray 10 is set in the rack tray set section 8A, the grip member 10d-1 is gripped to press the rack tray 10 to the side of the rack tray storing section 8c (FIG. 12-1). By gripping and pressing the grip member 10d-1, the rack tray 10 slidably travels on the rack tray storing section 8c (FIG. 12-2), and a rear end of the bottom section of the rack tray 10 travels to an upper side of the guide wall 8k. In this case, the guide wall 8k has a halfway inclined section, and the bottom section of the rack tray 10 slidably drops into the rack tray storing section 8c along the inclined section (FIG. 12-3). When the rack tray 10 is completely stored in the rack tray storing section 8c, a projection section 8h-1 projecting from the hole 8d is depressed by the weight of the rack tray 10 (FIG. 12-4). With this depression, the other end of the lock canceling lever 8g is pushed up by using the shaft 8f as a rotating axis, and a projection section 8h-2 at the other end of the lock canceling lever 8g projects from the hole 8d in the rack traveling direction. In this manner, one end of the dropout-preventing lever 10s of the rack dropout-preventing mechanism 10c is pushed up, and the other end of the dropout-preventing lever 10s is pushed down by using the shaft 10q as a rotating axis to cancel the lock state.

After the rack movement-preventing mechanism 10c is set in the rack tray set section 8A, the rack movement-preventing mechanism 10c is moved to the backmost section by gripping and pressing the handle section including the partition 10k and the partition 10l. After the rack movement-preventing mechanism 10c is moved, the push-out lever 8a built in the rack tray set section 8A is caused to travel to push the rack 9 out to the transport mechanism 8B, and the rack 9 is transported to the specimen dispenser 20 by the transport mechanism 8B. The rack tray set section 8A does not include the push-up section 10t serving as the lock canceling mechanism of the rack movement-preventing mechanism 10c. However, when the partition 10k of the rack movement-preventing mechanism 10c is only slightly pushed, the rack movement-preventing mechanism 10c is moved. For this reason, the rack tray set section 8A may include the push-up section 10t.

In the automatic analyzing apparatus 1, the rack tray 10 having the rack dropout-preventing mechanism 10b is used, and the rack transport system 8 according to Embodiment 1 in which the projection sections 8h serving as the lock canceling button of the lock canceling mechanism 8i on the rack tray set section 8A is caused to project near the guide wall 8k behind the rack tray set section 8A can slide the rack tray 9 to place the rack tray 9 on the rack tray set section 8A, and the rack tray 9 can be safely and easily placed. In Embodiment 1, the rack collecting section 8C includes the same lock canceling mechanism 8i as the lock canceling mechanism 8i of the rack tray set section 8A, and the projection section 8h serving as the lock canceling button of the rack dropout-preventing mechanism 10b on the rack collecting section 8C is caused to project near the guide wall 8k (see FIG. 7). Since the rack tray 10 on the rack collecting section 8C is to hold the rack 9 in which an almost empty specimen containers 9a is stored, it is lighter than the rack tray 10 placed on the rack tray set section 8A, and the necessity of slidably pulling up the rack tray 10 from the side when collecting is not high. Therefore, the lock canceling lever 8g of the lock canceling mechanism 8i need not have a length almost equal to the length in the rack traveling direction, and may be arranged near a rack transport entrance of the rack collecting section 8C.

In Embodiment 1, the rack transport system 8 having one rack tray set section 8A and one rack collecting section 8C has been described. However, the number of rack tray set sections and the number of rack collecting sections need only be equal to each other, and the system may have two or more rack tray set sections and two or more rack collecting sections. Furthermore, in FIG. 1, the automatic analyzing apparatus having the rack transport system 8 arranged on the right of the specimen dispenser 20 is illustrated. However, various modifications, made without departing from the objective of the present invention, such as a rack transport system in which the rack tray set section 8A is arranged near and on the right of the specimen dispenser 20, the rack collecting section 8C is arranged on the left, and the transport mechanism 8B is arranged in the lower section of the analyzing apparatus to connect the rack tray set section 8A and the rack collecting section 8C to each other can be used.

Figures 1, 13:
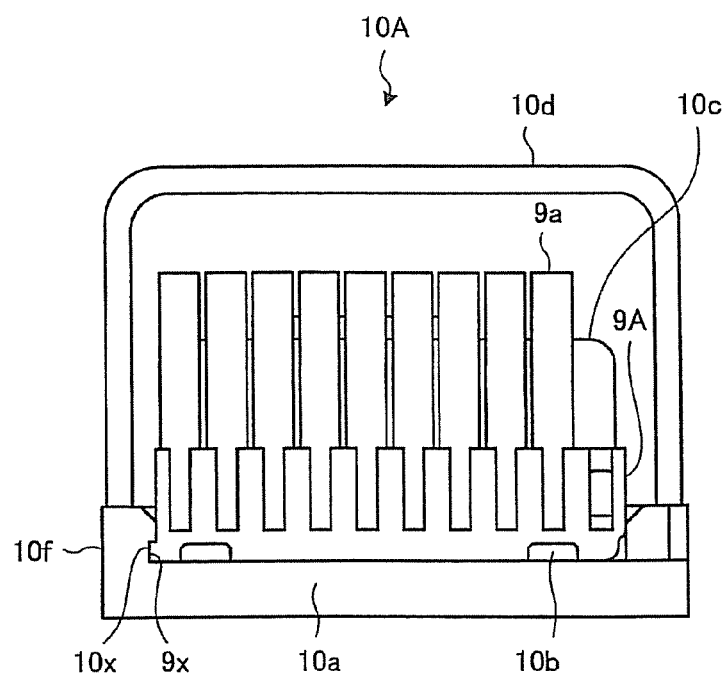
Figures 2, 13:
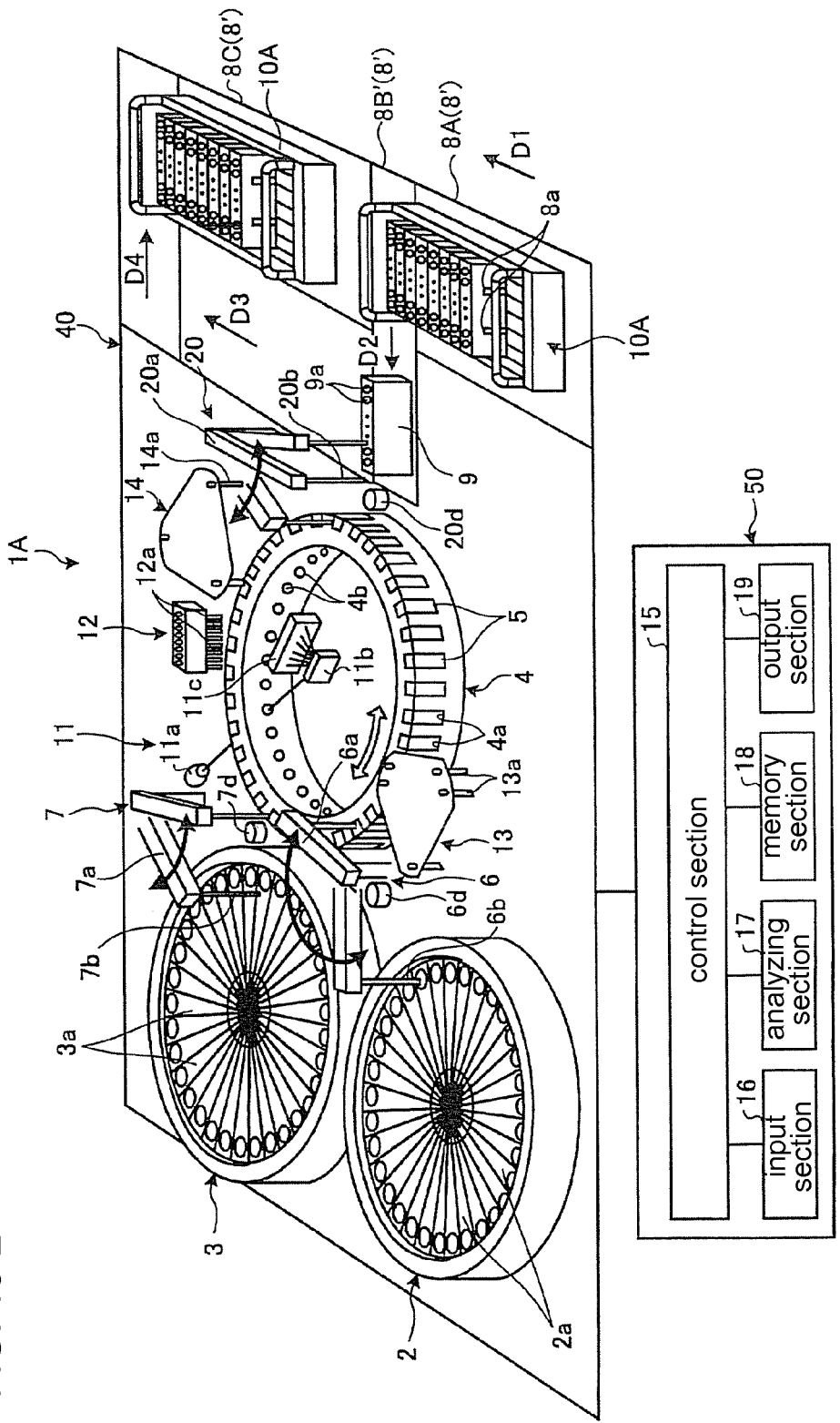
Figure 14:
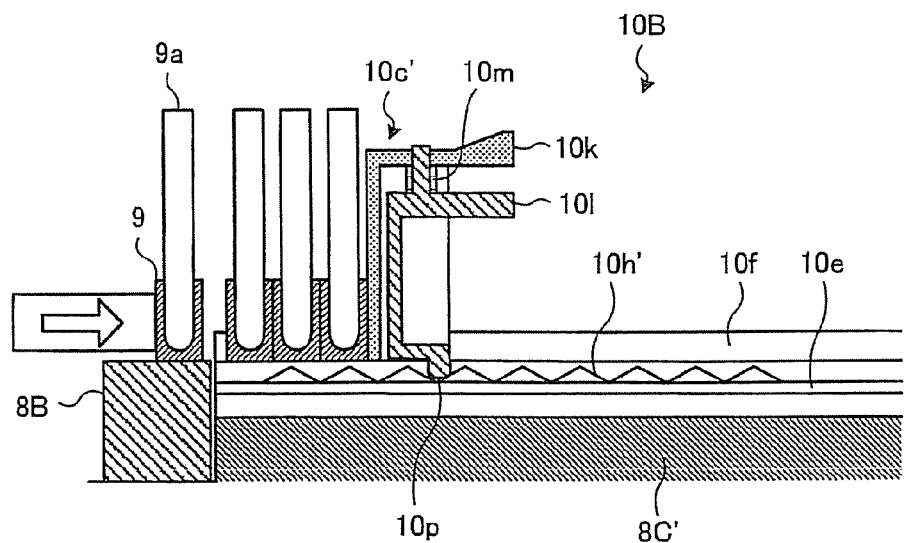
FIG. 14 is a sectional view showing Modification 2 of the rack tray according to Embodiment 1 together with a rack and a rack collecting section.

As a modification of the rack tray 10 used in Embodiment 1, as shown in FIG. 13-1, a rack tray 10a in which a side surface section, being in contact with a rack 9A, of the guide wall 10f of any one of the two sides parallel to the traveling direction of the rack 9 is hollowed out to form a fitting section 10x on the side surface section is illustrated. The fitting section 10x is formed on an entire lower section of the side surface being in contact with the substrate 10g of the guide wall 10f. On the rack tray 10a, the rack 9A having a projection section 9x fitted in the fitting section 10x is preferably stored. The rack tray 10a and the rack 9A are fitted through the fitting section 10x and the projection section 9x to make it possible to more stably transport the tray and set the tray in the apparatus. The fitting section 10x prevents the rack 9 from falling and moving together with the rack movement-preventing mechanism 10c. In FIG. 13-1, the fitting section 10x is a rectangular recessed section, and the projection section 9x is a rectangular projection section fitted in the recessed section. The fitting section 10x and the projection section 9x need only be fitted in each other, and trapezoidal shapes or the like may be employed. In use of the rack 9A and the rack tray 10a shown in FIG. 13-1, an automatic analyzing apparatus 1A including a rack transport system 8' as shown in FIG. 13-2 is used. Since the rack 9A and the rack tray 10a are horizontally asymmetrical because the projection section 9x and the fitting section 10x are formed, the rack 9A cannot be easily collected in the rack collecting section 8C when the rack trays 10a in the rack tray set section 8A and the rack collecting section 8C face each other. Therefore, when the rack 9A and the rack tray 10a are used, as shown in FIG. 13-2, the arrangements of the rack tray set section 8A and the rack collecting section 8C need to be changed to change the rack transport system such that the rack trays 10a are arranged in the same direction. As another modification, a rack tray 10b shown in FIG. 14 is illustrated. A rack movement-preventing mechanism 10c' does not have the shaft 10n, and inclinations of two slopes of the engagement section 10h' on the guide rail 10e are set to be equal to each other. When the inclinations of the slopes are set to be equal to each other, the rack movement-preventing mechanism 10c' can be moved in the forward or backward directions with the same force. When the rack 9 is pushed with a push-out lever (not shown) of the transport mechanism 8B, the projection 10p runs on the engagement section 10h' to make it possible to cancel the lock state.

Figure 15:
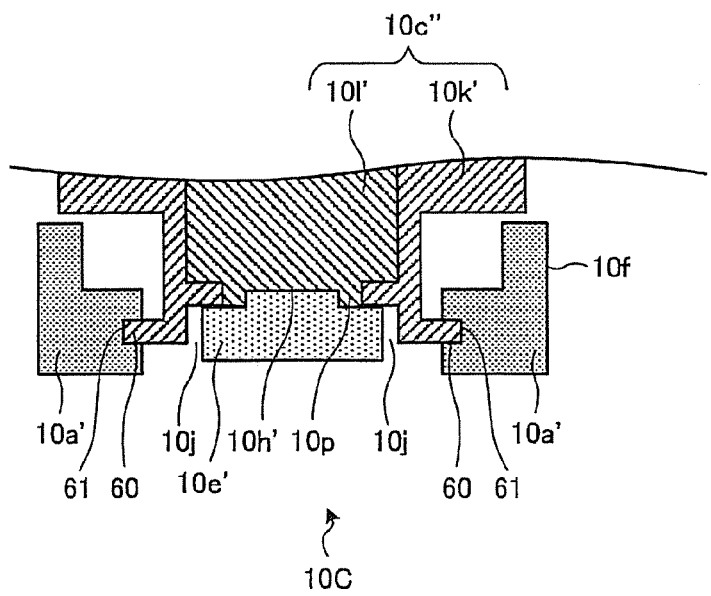
FIG. 15 is a cross-sectional view of an engagement section including a rack movement-preventing mechanism according to Modification 3 of Embodiment 1 and a guide rail.
Figures 1, 16:
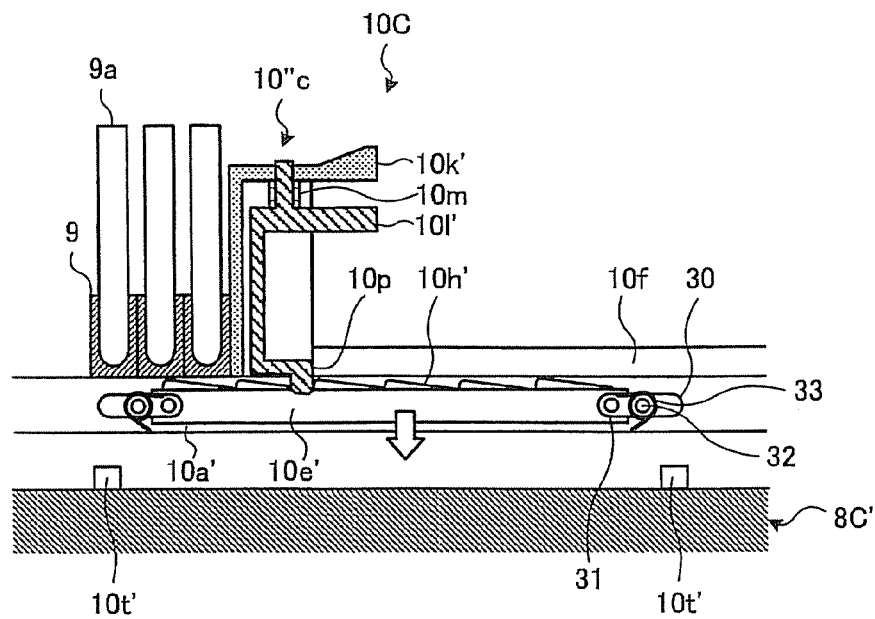
Figures 2, 16:
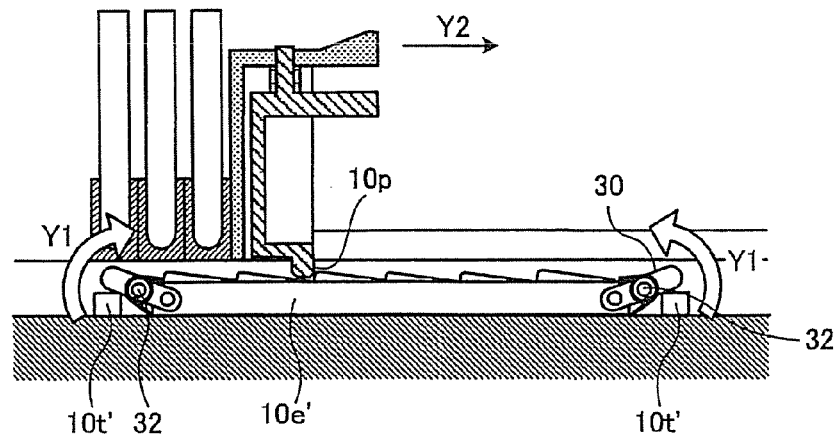

As a modification of the rack tray 10 used in Embodiment 1, a rack tray 10c shown in FIG. 15, FIG. 16-1, and FIG. 16-2 is illustrated. FIG. 15 is a cross-sectional view of an engagement section including a rack movement-preventing mechanism 10c'' and a guide rail 10e'. FIG. 16-1 and FIG. 16-2 are sectional views showing a rack tray 10c together with the rack 9 and a rack collecting section 8C'. The rack tray 10c is considerably different from the rack tray 10 of Embodiment 1 in that the guide rail 10e' is formed independently of the tray base 10a'. As shown in FIG. 15, the rack movement-preventing mechanism 10c'' does not have a shaft 10n (see FIG. 4). Therefore, the guide rail 10e' does not have the trench 10i through which the shaft 10n passes, and one engagement section 10h' is arranged at each position of the guide rail 10e'. The partition 10k' includes a projection 60 at the distal end thereof such that the partition 10k' is supported by a tray base 10a' not the guide rail 10e', and the projection 60 is engaged with an engagement section 61 formed on the tray base 10a'. As shown in FIG. 16-1, the guide rail 10e' is formed independently of the tray base 10a' and joined to the tray base 10a' through a joint member 30. A spring 33 that biases to rise up the guide rail 10e' is arranged between the joint member 30 and the guide rail 10e'. The guide rail 10e' is joined to the joint member 30 by the joint section 31 and supported on the tray base 10a' by a shaft 32 serving as a joint section between the joint member 30 and the tray base 10a'. The shape of the engagement section 10h' on the guide rail 10e' and the engagement between the engagement section 10h' and the projection 10p of the partition 10l' are the same as those in Embodiment 1 except that one engagement section 10h' is formed at each position on the guide rail 10e'. The partition 10k' or the partition 10l' is pushed to make it possible to move the rack movement-preventing mechanism 10c'' to the opening side of the rack tray 10c. However, movement in the opposite direction cannot be done until the partition 10k' and the partition 10l' are gripped and pressed from the upper and lower sides to cancel the engagement between the engagement section 10h' and the projection 10p. A description of the rack dropout-preventing mechanism 10b is omitted. However, the rack tray 10c includes the rack dropout-preventing mechanism 10b as in Embodiment 1.

A rack transport system using the rack tray 10c will be described below. The rack transport system using the rack tray 10c, like the rack transport system according to Embodiment 1, includes a rack tray set section, a transport mechanism, and a rack collecting section. However, the rack collecting section 8C' according to Embodiment 2, as shown in FIG. 16-1, includes, in place of the push-up section 10t of the shaft 10n, a push-up section 10t' that pushes up the joint member 30 of the rack tray 10c to push down the guide rail 10e'. The push-up section 10t' is arranged on the rack collecting section 8C' under the joint member 30. When the rack tray 10c is arranged in the rack collecting section 8C' from above, the push-up section 10t' is brought into contact with an outerside section of the joint member 30, as indicated by an arrow Y1 in FIG. 16-2, the push-up section 10t' pushes up the joint member 30 from the outside. With the push-up operation, the joint member 30 rotates by using the shaft 32 as a rotating axis to push down the guide rail 10e'. When the guide rail 10e' is pushed down, the engagement between the projection 10p at the distal end of the partition 10l' and the engagement section 10h' is canceled to make it possible to move the rack movement-preventing mechanism 10c'' in a backward direction (indicated by an arrow Y2).

Figure 17:
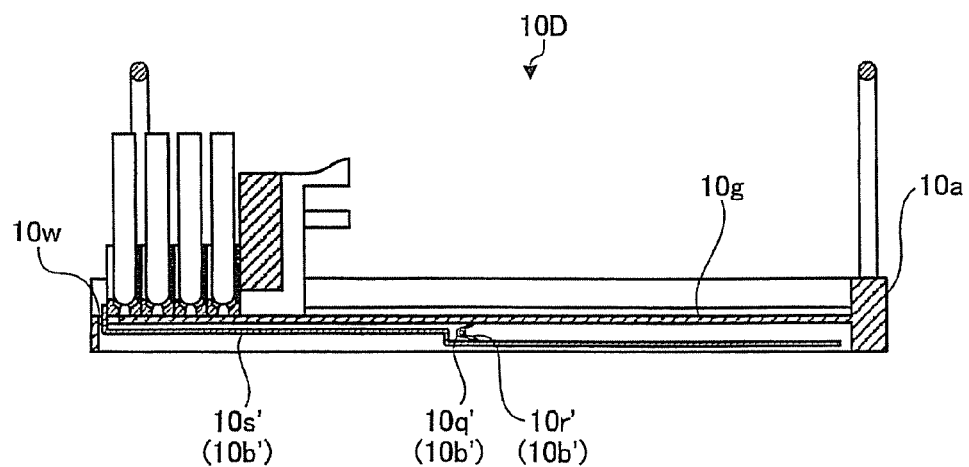
FIG. 17 is a sectional view of a rack tray according to Modification 4 of Embodiment 1.
Figure 18:
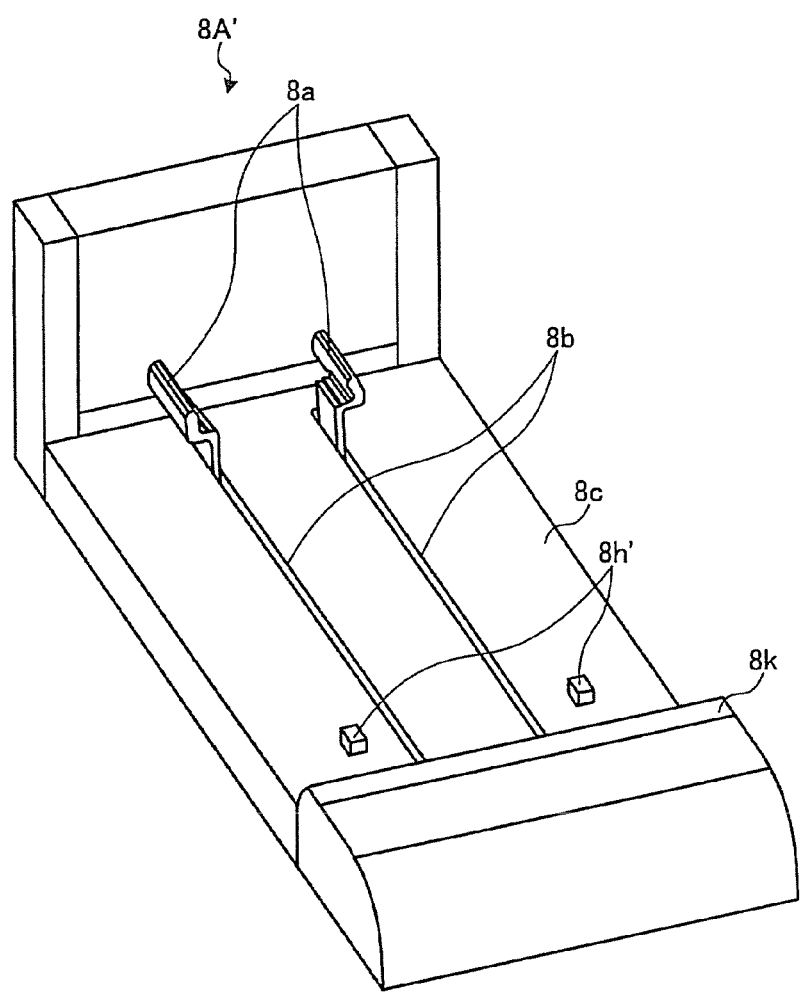
FIG. 18 is a perspective view of a rack tray set section according to Modification 4 of Embodiment 1.

Furthermore, as a modification of the rack tray 10 used in Embodiment 1, a rack tray 10D shown in FIG. 17 is illustrated. FIG. 17 is a sectional view of the rack tray 10D. A dropout-preventing lever 10s' of a rack dropout-preventing mechanism 10b' supported on the lower part of the substrate 10g of the tray base 10a by a shaft 10q' has a length almost equal to the length of the rack tray 10D in the rack traveling direction, and the shaft 10q' is arranged at the center section of the dropout-preventing lever 10s'. The spring 10r', like the rack tray 10, is biased upward to raise up an end of the dropout-preventing lever 10s' from the hole 10w. When the length of the dropout-preventing lever 10s' is made almost equal to the length of the rack tray 10D in the rack traveling direction, a complex lock canceling mechanism is not necessary. In a rack tray set section 8A' shown in FIG. 18, when a projection section 8h' is only formed near the guide wall 8k behind the rack tray storing section 8c, the rack dropout-preventing mechanism 10b' can be unlocked. In addition, since the rack tray 10D can be placed on the rack tray set section 8A' by sliding the rack tray 10D, the rack tray 10D can be safely and easily set.

Embodiment 2

Figure 19:
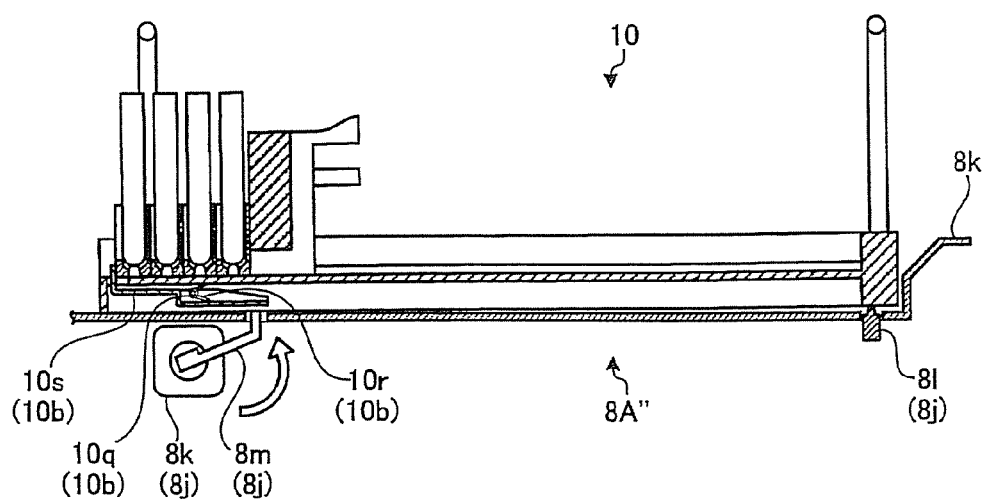
FIG. 19 is a sectional view of a rack tray set section according to Embodiment 2.

A rack transport system according to Embodiment 2 of the present invention will be described below with reference to the drawings. FIG. 19 is a sectional view of a rack tray set section 8A'' when the rack tray 10 is placed on the rack tray set section 8A''. The rack tray set section 8A'' includes a lock canceling mechanism 8j of the rack dropout-preventing mechanism 10b, and the lock canceling mechanism 8j has a lock canceling lever 8m, a sensor 8l, and a motor 8k. The lock canceling lever 8m is a lever that pushes up the dropout-preventing lever 10s of the rack dropout-preventing mechanism 10b, and is arranged on a transporting mechanism side of the rack tray set section 8A''. The sensor 8l is a sensor that, when the rack tray 10 in which a plurality of racks are held and stored is slid and placed on the rack tray set section 8A'', detects the placement, and is arranged near the guide wall 8k behind the rack tray set section 8A''. In Embodiment 2, the sensor 8l serves as a lock canceling button of the rack dropout-preventing mechanism 10b. The motor 8k pushes up the lock canceling lever 8m after the sensor 8l detects the placement of the rack tray 10 on the rack tray set section 8A''. Even in the rack transport system according to Embodiment 2, since the sensor 8l serving as the lock canceling button is arranged near the guide wall 8k, the rack tray 10 can be placed on the rack tray set section 8A'' by sliding the rack tray 10. For this reason, the rack tray 10D can be safely and easily set.

INDUSTRIAL APPLICABILITY

As described above, a rack transport system according to the present invention is effectively used in an automatic analyzing apparatus that optically measures a reaction between a specimen and a reagent to analyze components of the specimen. In particular, the rack transport system can be used in safe installation of a rack tray in which a plurality of racks supporting a plurality of specimen containers is arranged in an analyzing apparatus.

The invention claimed is:

1. A rack transport system using a rack tray having a rack dropout-preventing mechanism including a dropout-preventing lever, a shaft that supports the dropout-preventing lever on a rack tray, and a spring that biases the dropout-preventing lever upward about the shaft to cause the dropout-preventing lever to project from a rack tray opening to prevent a rack from dropping out, the rack transport system comprising:

a rack tray set section on which the rack tray that arranges and holds a plurality of racks supporting a plurality of specimen containers is placed;

a lock canceling mechanism of the rack dropout-preventing mechanism located on the rack tray set section, the lock canceling mechanism includes a lock canceling lever, a shaft that supports the lock canceling lever on a rack tray set section, and a spring that biases a lock canceling lever end on a guide wall side behind the rack tray set section to push up the lock canceling lever end, the lock canceling mechanism also includes a lock canceling button formed at a position where the rack tray that stores the plurality of racks supporting the plurality of specimen containers is slid to be able to be set in the rack tray set section;

a rack collecting section on which an empty rack tray is placed and the rack collecting section collects the racks supporting the specimen containers obtained after a dispensing operation is performed; and a transporting mechanism that transports the rack from the rack tray set section to a dispensing mechanism and transports the rack to the rack collecting section after a specimen is dispensed from the specimen container.

2. The rack transport system according to claim 1, wherein the rack tray set section includes a storing section that stores a rack tray, and the rack tray is slid from an upper side of a guide wall behind the storing section and placed on the rack tray set section.

3. The rack transport system according to claim 2, wherein the lock canceling button is formed near the guide wall behind the rack tray set section.

4. The rack transport system according to claim 1, configured to use a rack tray, wherein the dropout-preventing lever has a length almost equal to a length of the rack tray in a rack traveling direction.

5. The rack transport system according to claim 1, wherein the lock canceling lever has a length almost equal to a length of the rack tray set section in a rack traveling direction, wherein:

both ends of the lock canceling lever have projection sections that vertically rise, the projection section on the guide wall side behind the rack tray set section is the lock canceling button, and a hole to protrude the projection section therethrough is formed in the rack tray storing section of the rack tray set section.

6. The rack transport system according to claim 5, wherein the spring biases the lock canceling lever projection section on the guide wall side behind the rack tray set section to push up the lock canceling lever projection section to protrude the projection from the hole, and, when the rack tray that holds and stores a plurality of racks is slid to be placed on the rack tray set section, the projection section is pushed down by placing the rack tray, and the projection section at the other end is pushed up to cancel a lock state of a rack movement-preventing mechanism.

7. The rack transport system according to claim 1, wherein the lock canceling lever is arranged on a side of the transporting mechanism of the rack tray set section, and the lock canceling mechanism further includes:

a sensor that is arranged near the guide wall behind the rack tray set section and, when the rack tray that holds and stores a plurality of racks is slid and placed on the rack tray set section, detects the placement, and a motor that pushes up the lock canceling lever after the sensor detects the placement of the rack tray on the rack tray set section, wherein the sensor is the lock canceling button.

8. The rack transport system according to claim 1, wherein the rack collecting section includes the lock canceling mechanism of the rack dropout-preventing mechanism.

9. The rack transport system according to claim 1, wherein the rack tray includes a tray base that holds and stores a plurality of racks, and a rack movement-preventing mechanism that moves on the tray base and presses the plurality of racks arranged on the tray base to a side of the rack dropout-preventing mechanism.

10. The rack transport system according to claim 9, wherein the rack tray includes a guide rail having a plurality of engagement sections at positions corresponding to the number of racks held and stored on the tray base, and a locking section held by the rack movement-preventing mechanism is engaged with the engagement section to lock the movement of the rack.

11. The rack transport system according to claim 10, wherein the engagement section is a projection formed on the guide rail, the projection comprising first and second slopes, the first slope facing the rack tray opening, the second slope being on the opposite side of the projection from the first slope, wherein an inclination of the first slope is set to be high, and an inclination of the second slope is to be low.

12. The rack transport system according to claim 10, wherein the rack movement-preventing mechanism includes a handle section that pushes up the locking section, the handle section is gripped and pressed to push up the locking section to cancel the engagement with the engagement section, and the rack movement-preventing mechanism is moved.

13. The rack transport system according to claim 9, further comprising grip members arranged on two opposite sides of the tray base parallel to an arrangement direction of the racks on the tray base.

14. The transport system according to claim 10, wherein the guide rail is formed independently of the tray base, joined to the tray base by a joint member, and a spring that biases the guide rail to push up the guide rail is arranged between the joint member and the guide rail.

15. The transport system according to claim 9, wherein the tray base includes guide walls on three sides except for the opening in the rack traveling direction, and a guide wall of any one of two sides parallel to the traveling direction has a fitting section fitted on the rack formed on a side surface thereof.

16. The rack transport system according to claim 15, wherein the fitting section is configured to hold and store a rack having a projection section to be fitted in the fitting section.

17. The rack transport system according to claim 13, wherein the grip member arranged on an opening side of the rack in the traveling direction is arranged such that a holding section is offset from an arrangement position of the grip member.

18. The transport system according to claim 14, wherein the rack collecting section includes a lock canceling mechanism of the rack movement-preventing mechanism.

19. The rack transport system according to claim 18, wherein the lock canceling mechanism of the rack movement-preventing mechanism is a push-up member that pushes up the shaft of the rack tray.

20. The rack transport system according to claim 18, wherein the lock canceling mechanism of the rack movement-preventing mechanism is a push-up member that pushes up the joint member of the rack tray to push down the guide rail.

* * * * *

UNITED STATES PATENT AND TRADEMARK OFFICE
CERTIFICATE OF CORRECTION

PATENT NO.         : 8,658,096 B2
APPLICATION NO.    : 13/133764
DATED              : February 25, 2014
INVENTOR(S)        : Masahiro Kaiga It is certified that error appears in the above-identified patent and that said Letters Patent is hereby corrected as shown below:

On the Title Page:

In the Assignee Item (73), please replace "Beckman Coutler, Inc., Brea, CA (US)" with -- Beckman Coulter, Inc., Brea, CA (US) --

Signed and Sealed this
Third Day of June, 2014

Michelle K. Lee
*Deputy Director of the United States Patent and Trademark Office*